US012377037B2

(12) United States Patent
Johnson et al.

(10) Patent No.: US 12,377,037 B2
(45) Date of Patent: Aug. 5, 2025

(54) CLEAVABLE COMONOMER STRATEGY FOR ACCELERATING REMOVAL OF GEL NAIL POLISH

(71) Applicant: MASSACHUSETTS INSTITUTE OF TECHNOLOGY, Cambridge, MA (US)

(72) Inventors: Jeremiah A. Johnson, Boston, MA (US); Leticia C. Cardoso Da Costa, Somerville, MA (US); Elisabeth Prince, Waterloo (CA); Alexandra Johnson, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/718,795

(22) PCT Filed: Dec. 1, 2023

(86) PCT No.: PCT/US2023/082177
§ 371 (c)(1),
(2) Date: Jun. 11, 2024

(87) PCT Pub. No.: WO2024/119140
PCT Pub. Date: Jun. 6, 2024

(65) Prior Publication Data
US 2024/0423894 A1 Dec. 26, 2024

Related U.S. Application Data

(60) Provisional application No. 63/482,995, filed on Feb. 2, 2023, provisional application No. 63/429,438, filed on Dec. 1, 2022.

(51) Int. Cl.
*A61K 8/81* (2006.01)
*A61Q 3/02* (2006.01)

(52) U.S. Cl.
CPC .............. *A61K 8/8105* (2013.01); *A61Q 3/02* (2013.01); *A61K 2800/81* (2013.01)

(58) Field of Classification Search
CPC ..... A61K 8/8105; A61K 2800/81; A61Q 3/02
See application file for complete search history.

(56) References Cited

U.S. PATENT DOCUMENTS

| 7,326,447 B2 | 2/2008 | Taugerbeck et al. | |
| 2011/0256079 A1* | 10/2011 | Kozachek | A45D 31/00 424/61 |
| 2011/0274633 A1* | 11/2011 | Vu | A61K 8/8152 424/61 |
| 2013/0078207 A1* | 3/2013 | Sanbonmatsu | A45D 29/001 401/126 |
| 2016/0088919 A1 | 3/2016 | Oohashi | |
| 2022/0259173 A1 | 8/2022 | Rinsch et al. | |

FOREIGN PATENT DOCUMENTS

| WO | 2012005123 A1 | 1/2012 |
| WO | 2021205123 A1 | 10/2021 |
| WO | 20230154756 A2 | 8/2023 |

OTHER PUBLICATIONS

"Proximal," Definition 2, Merriam-Webster.com, Copyright 2024, Merriam-Webster, Incorporated, <https://www.merriam-webster.com/dictionary/proximal>, p. 1.*
H. Elliss et al., "Fully Degradable Polyacrylate Networks from Conventional Radical Polymerization Enabled by Thionolactone Addition," Macromolecules 2022, 55, 6695-6702.*
G. R. Kiel et al., "Cleavable Comonomers for Chemically Recyclable Polystyrene: A General Approach to Vinyl Polymer Circularity," J. Am. Chem. Soc. 2022, 144, 12979-12988.*
PCT International Search Report and Written Opinion completed by the ISA/US on Mar. 22, 2024 and issued in connection with PCT/US2023/082177.
Kiel, Gavin, et al., Cleavable Comonomers for Chemically Recyclable Polystyrene: A General Approach to Vinyl Polymer Circularity, J. Am. Chem. Soc. Jun. 28, 2022, vol. 144, pp. 12979-12988.
Ellis, et al., "Fully Degradable Polyacrylate Networks from Conventional Radical Polymerization Enabled by Thionolaclone Addition", Macromolecules, Jul. 25, 2022 (Jul. 25, 2022), vol. 55, pp. 6695-6702.
Smith, et al., "Radical Approach to Thioesler-Containing Polymers", Journal of the American Chemical Society, Jan. 12, 2019 (Jan. 12, 2019), vol. 141, vol. 4, pp. 1446-1451.
Bingham, et al., Biocompatibility and Physiological Thiolytic Biodegradability of Radically-made Thioester Functional Polymers, ChemRxiv. Cambridge: Cambridge Open Engage; 2022.
Bingham, et al., Degradable vinyl copolymers through thiocarbonyl addition-ring-opening (TARO) polymerization.
Gil, et al., Degradable Polystyrene via the Cleavable Comonomer Approach.
Pesenti, et al., 100th Anniversary of Macromolecular Science Viewpoint: Degradable Polymers from Radical Ring-Opening Polymerization: Latest Advances, New Directions, and Ongoing Challenges.
Spick, et al., Fully Degradable Thioester-functional Homo- and Alternating Copolymers.
Un Nisa, et al., Degradable Linear and Bottlebrush Thioester-Functional Copolymers through Atom-Transfer Radical Ring-Opening Copolymerization of a Thionolactone.
Agarwal, S.; Kumar, R.; Kissel, T.; Reul, R. Synthesis of Degradable Materials Based on Caprolactone and Vinyl Acetate Units Using Radical Chemistry. Polym. J 2009, 41 (8), 650-660.
Bailey, W. J.; Wu, S.-R.; Ni, Z. Synthesis and Free Radical Ring-Opening Polymerization of 2-Methylene-4-Phenyl-1,3-Dioxolane. Makromol. Chem. 1982, 183 (8), 1913-1920.

(Continued)

*Primary Examiner* — Monica A Shin
(74) *Attorney, Agent, or Firm* — Barnes & Thornburg, LLP

(57) ABSTRACT

The present invention provides polymer compositions for use in cosmetic nail polish compositions. More particularly, the present disclosure relates to the introduction of cleavable comonomer additives into an existing polymer composition to produce a chemically deconstructable composition. Methods and compositions for removing the nail polish composition are also disclosed.

18 Claims, 11 Drawing Sheets

(56) References Cited

OTHER PUBLICATIONS

Bingham, N. M.; Nisa, Q. un; Chua, S. H. L.; Fontugne, L.; Spick, M. P.; Roth, P. J. Thioester-Functional Polyacrylamides: Rapid Selective Backbone Degradation Triggers Solubility Switch Based on Aqueous Lower Critical Solution Temperature/Upper Critical Solution Temperature. ACS Appl. Polym. Mater. 2020, 2 (8), 3440-3449.

Brandmeier, V.; Feigel, M. A Macrocycle Containing Two Biphenyl and Two Alanine Subunits, Synthesis and Conformation in Solution. Tetrahedron 1989, 45 (5), 1365-1376.

Coates, G. W.; Getzler, Y. D. Y. L. Chemical Recycling to Monomer for an Ideal, Circular Polymer Economy. Nat. Rev. Mater. 2020, 5 (7), 501-516.

Dana, S.; Chowdhury, D.; Mandal, A; Chipem, F. A S.; Baidya, M. Ruthenium(II) Catalysis/Noncovalent Interaction Synergy for Cross-Dehydrogenative Coupling of Arene Carboxylic Acids. ACS Catal. 2018, 8 (11), 10173-10179.

Ebdon, J. R.; Flint, N. J. Synthesis of Water-Soluble Telechelic Methyl-Ketone-Ended Oligo-N, N-Dimethylacrylamides by the Ozonolysis of Poly(N, N-Dimethylacrylamide-Stat-2,3-Dimethylbutadiene)s. J. Polym. Sci. Part Polym. Chem. 1995, 33 (3), 593-597.

Ebdon, J. R.; Flint, N. J. Preparation of a,ω-Aldehyde-Ended Telechelic Methyl Methacrylate Oligomers by the Oxidative Cleavage of Statistical Methyl Methacrylate- Buta-1,3-Diene Copolymers. Eur. Polym. J 1996, 32 (3), 289-294.

Galanopoulo, P.; Gil, N.; Gigmes, D.; Lefay, C.; Guillaneuf, Y.; Lages, M.; Nicolas, J.; Lansalot, M.; D' Agosto, F. One-Step Synthesis of Degradable Vinylic Polymer-Based Latexes via Aqueous Radical Emulsion Polymerization. Angew. Chem. Int. Ed n/a (n/a).

Golemba, F. J.; Guillet, J. E. Photochemistry of Ketone Polymers. VII. Polymers and Copolymers of Phenyl Vinyl Ketone. Macromolecules 1972, 5 (2), 212-216.

Graessley, W. W. The Entanglement Concept in Polymer Rheology. In the Entanglement Concept in Polymer Rheology; Advances in Polymer Science; Springer: Berlin, Heidelberg, 1974; pp. 1-179.

Hanner, M. J.; McKelvy, M. L.; Sikkema, K.; Priddy, D. B. Photo-Degradable Polystyrene Part IV: Comparison of Photo-Degradation Efficiency of Random Styrene-Co-Vinyl Ketones (SVK) versus Blends of Polystyrene and SVK Concentrates. Polym. Degrad Stab. 1993, 39 (2), 235-239.

Ho, Ba Thanh, Timothy K. Roberts, and Steven Lucas. "An overview on biodegradation of polystyrene and modified polystyrene: the microbial approach." Critical reviews in biotechnology 38.2 (2018): 308-320.

Husted, K. E. L.; Shieh, P.; Lundberg, D. J.; Kristufek, S. L.; Johnson, J. A Molecularly Designed Additives for Chemically Deconstructable Thermosets without Compromised Thermomechanical Properties. ACS Macro Lett. 2021, 10 (7), 805-810.

Jackson, A W.; Reddy Mothe, S.; Chennamaneni, L. R.; van Herk, A; Thoniyot, P. Unraveling the History and Revisiting the Synthesis of Degradable Polystyrene Analogues via Radical Ring-Opening Copolymerization with Cyclic Ketene Acetals. Materials 2020, 13 (10), 2325.

Macosko, C. W.; Miller, D. R. A New Derivation of Average Molecular Weights of Nonlinear Polymers. Macromolecules 1976, 9 (2), 199-206.

Meijs, G. F.; Rizzardo, E.; Le, T. P. T.; Chen, Y.-C. Influence of Thionoesters on the Degree of Polymerization of Styrene, Methyl Acrylate, Methyl Methacrylate and Vinyl Acetate. Makromol. Chem. 1992, 193 (2), 369-378.

Miyagawa, M.; Akiyama, T. Tishchenko Reaction Using Substoichiometric Amount of Metallic Zinc. Chem. Lett. 2017, 47 (1), 78-81.

Modern Styrenic Polymers: Polystyrenes and Styrenic Copolymers; Scheirs, J., Priddy, D. B., Eds.; Scheirs, J., Series Ed.; Wiley Series in Polymer Science; John Wiley & Sons, Ltd: Chichester, UK, 2003.

Neto, N. S.; Jones, D. J.; Wong, W. W. H. Theoretical Aspects of Iterative Coupling for Linear Oligomers and Polymers. Macromol. Theory Simul. 2020, 29 (2), 1900048.

Perrier, Sebastien, and Pittaya Takolpuckdee. "Macromolecular design via reversible addition—fragmentation chain transfer (RAFT)/xanthates (MADIX) polymerization." Journal of Polymer Science Part A: Polymer Chemistry 43.22 (2005): 5347-5393.

PCT International Search Report and Written Opinion for Application No. PCT/US2023/62223 dated of mailing Jul. 19, 2023.

Rimmer, S.; Ebdon, J. R. Synthesis of Telechelic Oligostyrenes by the Ozonoloysis of Poly(Styrene-Stat-Butadiene): Protection of Styrene Units against Ozone Attack by the Use of Di-N-Alkyl Amides as Sacrificial Ozone Scavengers. J Polym. Sci. Part Polym. Chem. 1996, 34 (17), 3573-3583.

Sawaguchi, T.; Seno, M. Controlled Thermal Degradation of Polystyrene Leading to Selective Formation of End-Reactive Oligomers. J Polym. Sci. Part Polym. Chem. 1998, 36 (1), 209-213.

Sawaguchi, T.; Seno, M. Synthesis of Multiblock Copolymers of a,ω-Dihydrosilylpolydimethylsiloxane with a, ω-Diisopropenyloligopropylenes with Different Stereoregularities. J. Polym. Sci. Part Polym. Chem. 1996, 34 (17), 3625-3629.

Schmid, S. A; Abbel, R.; Schenning, A. P. H.; Meijer, E.W.; Sijbesma, R. P.; Herz, L. M. Analyzing the Molecular Weight Distribution in Supramolecular Polymers. J. Am. Chem. Soc. 2009, 131 (48), 17696-17704.

Shieh, P.; Zhang, W.; Husted, K. E. L.; Kristufek, S. L.; Xiong, B.; Lundberg, D. J.; Lem, J.; Veysset, D.; Sun, Y.; Nelson, K. A; Plata, D. L.; Johnson, J. A Cleavable Comonomers Enable Degradable, Recyclable Thermoset Plastics. Nature 2020, 583 (7817), 542-547.

Shieh, P.; Hill, M. R.; Zhang, W.; Kristufek, S. L.; Johnson, J. A Clip Chemistry: Diverse (Bio)(Macro)Molecular and Material Function through Breaking Covalent Bonds. Chem. Rev. 2021, 121 (12), 7059-7121.

Shim, Sang Eun, et al. "Fully crosslinked poly (styrene-co-divinylbenzene) microspheres by precipitation polymerization and their superior thermal properties." Journal of Polymer Science Part A: Polymer Chemistry 42.4 (2004): 835-845.

Tardy, A; Nicolas, J.; Gigmes, D.; Lefay, C.; Guillaneuf, Y. Radical Ring-Opening Polymerization: Scope, Limitations, and Application to (Bio)Degradable Materials. Chem. Rev. 2017, 117 (3), 1319-1406.

Tardy, A; Honore, J.-C.; Tran, J.; Siri, D.; Delplace, V.; Bataille, I.; Letourneur, D.; Perrier, J.; Nicoletti, C.; Maresca, M.; Lefay, C.; Gigmes, D.; Nicolas, J.; Guillaneuf, Y. Radical Copolymerization of Vinyl Ethers and Cyclic Ketene Acetals as a Versatile Platform to Design Functional Polyesters. Angew. Chem. Int. Ed 2017, 56 (52), 16515-16520.

Tsarevsky, N. V.; Matyjaszewski, K. Reversible Redox Cleavage/Coupling of Polystyrene with Disulfide or Thiol Groups Prepared by Atom Transfer Radical Polymerization. Macromolecules 2002, 35 (24), 9009-9014.

Wang, W.; Zhou, Z.; Sathe, D.; Tang, X.; Moran, S.; Jin, J.; Haeffner, F.; Wang, J.; Niu, J. Degradable Vinyl Random Copolymers via Photocontrolled Radical Ring-Opening Cascade Copolymerization**. Angew. Chem. Int. Ed 2022, e202113302.

Whittaker, M. R.; Goh, Y.-K.; Gemici, H ; Legge, T. M.; Perrier, S.; Monteiro, M. J. Synthesis of Monocyclic and Linear Polystyrene Using the Reversible Coupling/Cleavage of Thiol/Disulfide Groups. Macromolecules 2006, 39 (26), 9028-9034.

Wickel, H.; Agarwal, S. Synthesis and Characterization of Copolymers of 5,6-Benzo-2-Methylene-1,3-Dioxepane and Styrene. Macromolecules 2003, 36 (16), 6152-6159.

Worrell, et al., User's Guide to the Thiol-Thioester Exchange in Organic Media: Scope, Limitations, and Applications in Material Science. Polym. Chem. 2018, 9 (36), 4523-4534.

Yardley, R. E.; Kenaree, A. R.; Gillies, E. R. Triggering Depolymerization: Progress and Opportunities for Self-Immolative Polymers. Macromolecules 2019, 52 (17), 6342-6360.

Yuan, J.- Y.; Pan, C.-Y. "Living" Free Radical Ring-Opening Copolymerization of 4,7-Dimethyl-2-Methylene-1,3-Dioxepane and Conventional Vinyl Monomers. Eur. Polym. J 2002, 38 (10), 2069-2076.

(56) References Cited

OTHER PUBLICATIONS

Zhang, X.-S.; Zhang, Y.-F.; Li, Z.-W.; Luo, F.-X.; Shi, Z.-J. Synthesis of Dibenzo[c,e]Oxepin-5(7H)-Ones from Benzyl Thioethers and Carboxylic Acids: Rhodium-Catalyzed Double C—H Activation Controlled by Different Directing Groups. Angew. Chem. Int. Ed. 2015, 54 (18), 5478-5482.
www.Matweb.com/Search/DataSheet.Aspx?MatGUID=1c4 | e50c2e324e00b0c4e4 | 9ca78 0304&ckck=|.

\* cited by examiner

CLEAVABLE COMONOMER STRATEGY FOR ACCELERATING REMOVAL OF GEL NAIL POLISH

CROSS REFERENCE TO RELATED APPLICATIONS

This application is a U.S. national counterpart application of International Patent Application No. PCT/US2023/082177, entitled "CLEAVABLE COMONOMER STRATEGY FOR ACCELERATING REMOVAL OF GEL NAIL POLISH," filed Dec. 1, 2023, which claims priority to and the benefit of U.S. Provisional Patent Application Nos. 63/429,438 and 63/482,995, filed Dec. 1, 2022, and Feb. 2, 2023, respectively, the content of which are incorporated by reference herein in their entireties.

TECHNICAL FIELD

The present disclosure relates to a gel nail polish, and more particularly to a gel nail polish polymer composition and its uses, and degradation for easy removal.

BACKGROUND OF INVENTION

Gel nail polish is a popular cosmetic item that consumers use to enhance the appearance and durability of their nails. Gel polish is typically made up of monomers and a photo initiator that, when exposed to ultraviolet (UV) irradiation, initiates polymerization (i.e. cures the composition) into a resistant network coating on the nail. The coating is long-lasting and more resistant to chipping and scratching than typical nail polish.

Gel nail polish is often used to lengthen the nail or provide a stronger top layer over the natural nail. Consumers may utilize gel polish at-home or at a salon. When a consumer wants to remove the polish, their removal options are limited and inefficient. The "soak-off" method usually requires over 10 minutes and exposes the fingertips to damaging amounts of acetone. Additionally, any scratching to remove the polish can damage the consumer's nail plate. Alternatively, a nail salon can use a mechanical sanding method to remove the gel polish, but salon removal comes at a cost to the consumer. There remains, therefore, a need to develop a gel nail polish that is easier to remove while obtaining the aforementioned benefits of gel polish.

SUMMARY

In a first aspect, the present disclosure relates to a polymer composition comprising a first monomer, a second monomer, and a third monomer. The first monomer is of a Formula I or a tautomer or salt thereof, the Formula I being:

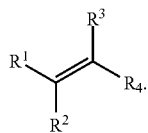

(I)

The second monomer comprises two or more non-aromatic unsaturated carbon-carbon bonds; and the third monomer is:

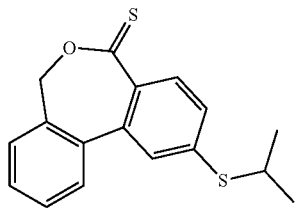 [SMILES: CC(C)Sc1ccc2c(c1)-c1ccccc1COC2=S]

or a tautomer or salt thereof.

In some embodiments, the first monomer is a methacrylate. In some embodiments, a cosmetic formulation comprises the polymeric composition and a cosmetically acceptable excipient.

In some embodiments, the first, second, and third monomers exist in about equal amounts in the polymer composition. In certain embodiments, the third monomer comprises 1-10 wt % of the polymer composition.

In certain embodiments, the polymer composition may be prepared by a method comprising mixing the first, second, and third monomers to form a first mixture; and irradiating the first mixture with ultraviolet light. In some embodiments, the third monomer is added subsequently to a mixture of the first and second monomers to create the polymer composition.

In some embodiments, the method further comprises the step of mixing the first, second, and third monomers on a proximal surface of the first mixture to form a second mixture; and irradiating the second mixture with ultraviolet light. In some embodiments, a method of coloring a human's nails comprises applying the polymer composition to a nail bed.

In another aspect, a method of removing a cosmetic, polymer composition from a nail bed comprises immersing a nail bed coated with a polymer composition in a removal solution comprising cysteine and an aqueous base, the polymer composition comprising a first monomer, a second monomer, and a third monomer of Formula III or a tautomer or salt thereof

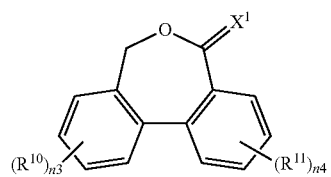

(III)

wherein $X^1$ is S or O;

each instance of $R^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R$^b$)$_2$, —C(=NR$^b$)R$^b$, —C(=NR$^b$)OR$^b$, —C(=NR$^b$)SR$^b$, —C(=NR$^b$)N(R$^b$)$_2$, —S(=O)R$^b$, —S(=O)OR, —S(=O)SR, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR$^b$, —OC(=O)N(R$^b$)$_2$, —OC(=NR)R$^b$, —OC(=NR$^b$)OR$^b$, —OC(=NR$^b$)SR$^b$, —OC(=NR$^b$)N(R)$_2$, —OS(=O)R$^b$, —OS(=O)OR, —OS(=O)SR$^b$, —OS(=O)

N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR$^b$, —SC(=O)SR$^b$, —SC(=O)N(R$^b$)$_2$, —SC(=NR$^b$)R$^b$, —SC(=NR$^b$)OR$^b$, —SC(=NR$^b$)SR$^b$, —SC(=NR$^b$)N(R$^b$)$_2$, —NR$^b$C(=O)R$^b$, —NR$^b$C(=O)OR$^b$, —NR$^b$C(=O)SR$^b$, —NR$^b$C(=O)N(R$^b$)$_2$, NR$^b$C(=NR$^b$)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R$^b$, —NR$^b$S(=O)OR$^b$, NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, Si(R$^b$)(OR$^b$)$_2$, Si(OR$^b$)$_3$, OSi(R$^b$)$_3$, OSi(R$^b$)$_2$OR$^b$, OSi(R$^b$)(OR$^b$)$_2$, or OSi(OR$^b$)$_3$;

each instance of R$^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R$^b$)$_2$, —C(=NR$^b$)R$^b$, C(=NR$^b$)OR$^b$, C(=NR$^b$)SR$^b$, C(=NR$^b$)N(R$^b$)$_2$, S(=O)R$^b$, S(=O)OR$^b$, S(=O)SR, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR$^b$, —OC(=O)N(R$^b$)$_2$, —OC(=NR)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR$^b$, —SC(=O)SR$^b$, —SC(=O)N(R$^b$)$_2$, —SC(=NR$^b$)R$^b$, —SC(=NR$^b$)OR$^b$, —SC(=NR$^b$)SR$^b$, —SC(=NR)N(R)$_2$, —NR$^b$C(=O)R$^b$, —NR$^b$C(=O)OR$^b$ NR$^b$C(=O)SR$^b$, —NR$^b$C(=O)N(R$^b$)$_2$, —NR$^b$C(=NR$^b$)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR$^b$, —OSi(R$^b$)(OR$^b$)$_2$, or OSi(OR$^b$)$_3$;

n3 is 0, 1, 2, 3, or 4, n4 is 0, 1, 2, 3, or 4, and at least one of n3 and n4 is 1, 2, 3, or 4; provided that no instance of R$^{10}$ and R$^{11}$ comprises one or more non-aromatic unsaturated CC bonds.

In some embodiments, the method further comprises immersing the polymer composition in the removal solution for a period of about 5 to 10 minutes. In some embodiments, the removal solution further comprises acetone. In certain embodiments, the third monomer is of Formula IV or a tautomer or salt thereof

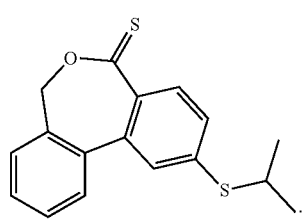

(IV)

In some embodiments, the first monomer is of Formula I or a tautomer or salt thereof

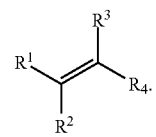

(I)

In certain embodiments, the removal solution comprises about 0.1 to 2 mM of cysteine. In some embodiments, the removal solution comprises about 0.1 to 0.5 mM of cysteine. In some embodiments, the removal solution has a pH of about 8-10.

In a third aspect, the present disclosure relates to a nail polish kit comprising a removal solution comprising cysteine and an aqueous base, instructions for using the nail polish kit, and nail polish composition further comprising a first monomer, a second monomer, and a third monomer of Formula III or a tautomer or salt thereof:

(III)

wherein X$^1$ is S or O;

each instance of R$^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R$^b$)$_2$, —C(=NR$^b$)R$^b$, C(=NR$^b$)OR$^b$, C(=NR$^b$)SR$^b$, C(=NR$^b$)N(R$^b$)$_2$, S(=O)R$^b$, S(=O)OR$^b$, S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR$^b$, —OC(=O)N(R$^b$)$_2$, —OC(=NR$^b$)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR, —SC(=O)SR$^b$, —SC(=O)N(R$^b$)$_2$, —SC(=NR$^b$)R, —SC(=NR$^b$)OR$^b$, —SC(=NR$^b$)SR$^b$, —SC(=NR$^b$)N(R$^b$)$_2$, —R$^c$(=O)R$^b$ NR$^b$C(=O)OR$^b$, —NR$^b$C(=O)SR$^b$, —NR$^b$C(=O)N(R$^b$)$_2$, —NR$^b$C(=NR$^b$)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR$^b$, —OSi(R$^b$)(OR$^b$)$_2$, or —OSi(OR$^b$)$_3$;

each instance of R$^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R$^b$)$_2$, —C(=NR$^b$)R, —C(=NR$^b$)OR$^b$, —C(=NR$^b$)SR$^b$, —C(=NR$^b$)N(R$^b$)$_2$, —S(=O)R$^b$, —S(=O)OR$^b$, —S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR$^b$, —OC(=O)N(R$^b$)$_2$, —OC(=NR$^b$)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR, —SC(=O)SR$^b$, —SC(=O)N(R$^b$)$_2$, —SC(=NR$^b$)R$^b$, —SC(=NR$^b$)OR$^b$, —SC(=NR$^b$)SR$^b$, —SC(=NR$^b$)N(R)$_2$, —NR$^b$C(=O)R$^b$ NR$^b$C(=O)OR$^b$ NR$^b$C(=O)SR$^b$, —NR$^b$C(=O)N(R$^b$)$_2$, —NR$^b$C(=NR$^b$)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR$^b$, —OSi(R$^b$)(OR$^b$)$_2$, or —OSi(OR$^b$)$_3$; and n3 is 0, 1, 2, 3, or 4, n4 is 0, 1, 2, 3, or 4, and at least one of n3 and n4 is 1, 2, 3, or 4; provided that no instance of R$^{10}$ and R$^{11}$ comprises one or more non-aromatic unsaturated CC bonds.

In some embodiments, the third monomer is Formula IV or tautomer or salt thereof

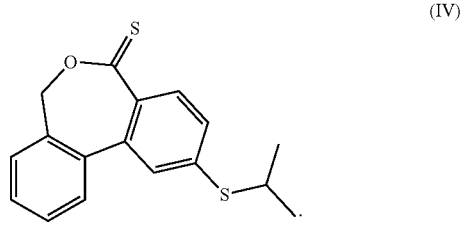 [SMILES: CC(C)Sc1ccc2c(c1)-c1ccccc1COC2=S]

(IV)

In certain embodiments, the removal solution comprises about 0.1 to 2 mM of cysteine. In some embodiments, the removal solution comprises about 0.1 to 0.5 mM of cysteine. In some embodiments, the nail polish composition comprises the first, second, and third monomer in about equal amounts in the polymer composition.

DEFINITIONS

Figure 1:
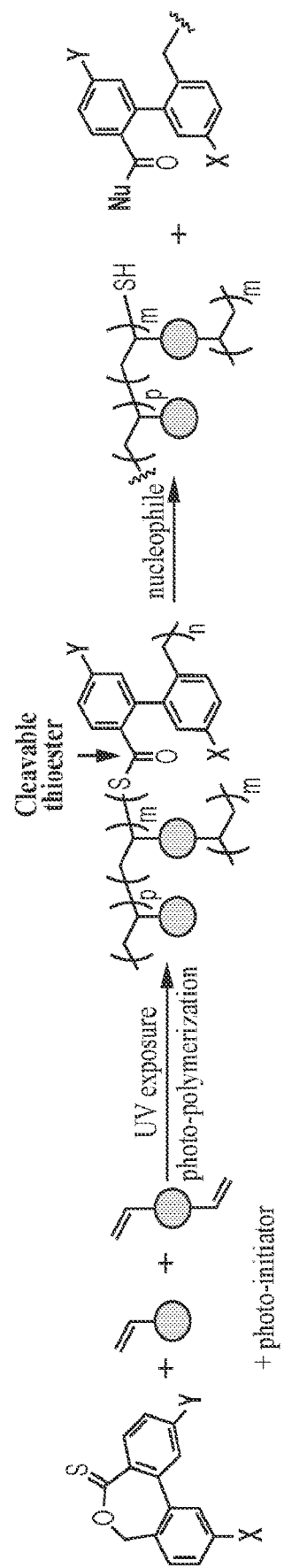
FIG. 1 depicts the polymerization of an embodiment of the invention

For purposes of interpreting this specification, the following abbreviations, terms and definitions will apply and whenever appropriate, terms used in the singular will also include the plural and vice versa. In the event that any definition set forth below conflicts with any document incorporated herein by reference, the definition set forth below shall control.

Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, NY, 1962); and Wilen, Tables of Resolving Agents and Optical Resolutions p. 268 (E. L. Eliel, Ed., Univ. of Notre Dame Press, Notre Dame, IN 1972). The present disclosure additionally encompasses compounds described herein as individual isomers substantially free of other isomers, and alternatively, as mixtures of various isomers.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in ≡CH). The moieties =$CH_2$ and =CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C=C double bonds in all the rings of the carbocyclic ring system that are not aromatic or heteroaromatic. Carbocyclyl including one or more (e.g., two or three, as valency permits) C=C double bonds in the carbocyclic ring is referred to as "cycloalkenyl." Carbocyclyl including one or more (e.g., two or three, as valency permits) C≡C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-13 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include azirdinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thienyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepanyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments alkyl, carbocyclyl, heterocyclyl, aryl, and heteroaryl groups, as defined herein, are optionally substituted (e.g., "substituted" or "unsubstituted" alkyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^a$, —OC(=O)R$^a$, —OCO$_2$R$^{aa}$, —C(=O)N(R$^{bb}$)$_2$, —OC(=O)N(R$^{bb}$)$_2$, —NR$^b$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)

OR$^{aa}$, —C(=NR$^{bb}$)N(R$^{bb}$)$_2$, —OC(=NR$^b$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$—NR$^{bb}$P(=O)(OR$^{cc}$)$_2$—NR$^{bb}$P(=O)(N(R$^{bb}$)$_2$)$_2$, P(R$^{cc}$)$_2$, —P(OR$^{cc}$)$_2$, —P(R$^{cc}$)$_3$+X$^-$, —P(OR$^{cc}$)$_3$+X$^-$, —P(R$^{cc}$)$_4$, —P(OR$^{cc}$)$_4$, —OP(R$^{cc}$)$_2$, —OP(R$^{cc}$)$_3$+X$^-$, —OP(OR$^{cc}$)$_2$, —OP(OR$^{cc}$)$_3$+X$^-$, —OP(R$^{cc}$)$_4$, —OP(OR$^{cc}$)$_4$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

wherein X is a counterion; or two geminal hydrogens on a carbon atom are replaced with the group =O, =S, =NN(R$^{bb}$)$_2$, NNR$^{bb}$C(=O)R$^{aa}$=NNR$^{bb}$C(=O)OR, =NNR$^{bb}$ S(=O)$_2$R, =NR$^{bb}$, or =NOR$^{cc}$;

each instance of R$^a$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R')$_2$, —SO$_2$R$^{cc}$, —SO$_2$OR$^c$, —SOR$^{aa}$, —C(=S)N(R$^{cc}$)$_2$, C(=O)SR$^{cc}$, —C(=S)SR$^{cc}$, —P(=O)(R$^{aa}$)$_2$, —P(=O)(OR$^{cc}$)$_2$, —P(=O)(N(R$^c$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^d$d groups; wherein X is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^f$)$_2$, —N(R$^f$)$_3$+X$^-$, —N(OR$^{ee}$)Re, —SH, —SR$^{ee}$, —SSR$^{ee}$, —C(=O)R$^{ee}$, —CO$_2$H, —CO$_2$R$^{cc}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{aa}$, —C(=NR$^{ff}$)N(R$^{ff}$)$_2$, —OC(=NR$^{ff}$)N(R$^{ee}$)$_2$, —NR$^b$C(=NR$^{ff}$)N(R$^{ee}$)$_2$, —NR$^{ee}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, hetero C$_{1-6}$ alkyl, hetero C$_{2-6}$alkenyl, hetero C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^f$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, hetero C$_{2-6}$alkenyl, hetero C$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP (=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

In certain embodiments, the carbon atom substituents are independently halogen, substituted (e.g., substituted with one or more halogen) or unsubstituted $C_{1-6}$ alkyl, —O$R^{aa}$, S$R^{aa}$, —N($R^{bb}$)$_2$, —CN, —SCN, —NO$_2$, —C(=O)$R^{aa}$, —CO$_2R^{aa}$, —C(=O)N($R^{bb}$)$_2$, —OC(=O)$R^{aa}$, —OCO$_2R^{aa}$, —OC(=O)N($R^{bb}$)$_2$, —NR$^{bb}$C(=O)$R^{aa}$, —NR$^{bb}$CO$_2R^{aa}$, or —NR$^{bb}$C(=O)N($R^{bb}$)$_2$. In certain embodiments, the carbon atom substituents are independently halogen, substituted (e.g., substituted with one or more halogen) or unsubstituted $C_{1-6}$ alkyl, —O$R^a$, —S$R^{aa}$, —N($R^{bb}$)$_2$, —CN, —SCN, —NO$_2$, —C(=O)$R^{aa}$, —CO$_2R^{aa}$, —C(=O)N($R^{bb}$)$_2$, —OC(=O)$R^{aa}$, —OCO$_2R^{aa}$, —OC(=O)N($R^{bb}$)$_2$, —NR$^{bb}$C(=O)$R^{aa}$, —NR$^{bb}$CO$_2R^{aa}$, or —NR$^{bb}$C(=O)N($R^{bb}$)$_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group. In certain embodiments, the carbon atom substituents are independently halogen, substituted (e.g., substituted with one or more halogen) or unsubstituted $C_{1-6}$ alkyl, —O$R^{aa}$, —S$R^a$, —N($R^{bb}$)$_2$, —CN, —SCN, or —NO$_2$. In certain embodiments, the carbon atom substituents are independently halogen, substituted (e.g., substituted with one or more halogen moieties) or unsubstituted $C_{1-6}$ alkyl, —O$R^{aa}$, —S$R^{aa}$, —N($R^{bb}$)$_2$, —CN, —SCN, or —NO$_2$, wherein $R^{cc}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$—, ClO$_4^-$, OH$^-$, H$_2$PO$_4^-$, HCO$_3^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$, PF$_4$, PF$_6$—, AsF$_6$, SbF$_6$, B[3,5—(CF$_3$)$_2$C$_6$H$_3$]$_4^-$, B(C$_6$F$_5$)$_4$, BPh$_4$, Al(OC(CF$_3$)$_3$)$_4$—, and carborane anions (e.g., CB$_{11}$H$_{12}$— or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^c$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a nitrogen protecting group. In certain embodiments, the nitrogen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a nitrogen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^c$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^c$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Amide nitrogen protecting groups (e.g., —C(=O)$R^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-10 doethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include p-toluenesulfonamide (Ts), benzenesulfonamide, 2,3,6,  -trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted C$_{1-6}$ alkyl, —C(=O)R$^{aa}$, —CO$_2$R$^{cc}$, —C(=O)N(R$^{bb}$)$_2$, or an oxygen protecting group. In certain embodiments, the oxygen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or an oxygen protecting group, wherein R$^{aa}$ is hydrogen, substituted (e.g., substituted with one or more halogen) or unsubstituted C$_{1-6}$ alkyl, or an oxygen protecting group when attached to an oxygen atom; and each R$^{bb}$ is independently hydrogen, substituted (e.g., substituted with one or more halogen) or unsubstituted C$_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —$R^{aa}$, —$N(R^{bb})_2$, —$C(=O)SR^{aa}$, —$C(=O)R^{aa}$, $CO_2R^{aa}$, $C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3+X^-$, —$P(OR^{cc})_2$, —$P(OR^{cc})_3+X^-$, —$P(=O)(R^{aa})_2$, —$P(=O)(OR^{cc})_2$, and —$P(=O)(N(R^{bb})_2)_2$, wherein X, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio)ethyl carbonate (Peoc), alkyl isobutyl carbonate, alkyl vinyl carbonate alkyl allyl carbonate, alkylp-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or a sulfur protecting group. In certain embodiments, the sulfur atom substituents are independently substituted (e.g., substituted with one or more halogen) or unsubstituted $C_{1-6}$ alkyl, —$C(=O)R^{aa}$, —$CO_2R^{aa}$, —$C(=O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^b)R^{aa}$, —$C(=NR^{bb})OR^{aa}$, —$C(=NR^b)N(R^{bb})_2$, —$S(=O)R^{aa}$, —$SO_2R^{aa}$, —$Si(R^{aa})_3$, —$P(R^{cc})_2$, —$P(R^{cc})_3+X^-$, —$P(OR^{cc})_2$, —$P(OR^{cc})_3X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamine, pixyl, and haloformates. In some cases, the leaving group is a sulfonic acid ester, such as toluenesulfonate (tosylate, -OTs), methanesulfonate (mesylate, -OMs), p-bromobenzene sulfonyloxy (brosylate, -OBs), —OS(=O)$_2$(CF$_2$)$_3$CF$_3$ (nonaflate, -ONf), or trifluoromethane sulfonate (triflate, -OTf). In some cases, the leaving group is a brosylate, such asp-bromo benzenesulfonyloxy. In some cases, the leaving group is a nosylate, such as 2-nitrobenzene sulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

"Compounds" include, e.g., small molecules and macromolecules. Macromolecules include, e.g., polymers, peptides, proteins, carbohydrates, monosaccharides, oligosaccharides, polysaccharides, nucleoproteins, mucoproteins, lipoproteins, synthetic polypeptides or proteins, glycoproteins, steroids, nucleic acids, DNAs, RNAs, nucleotides, nucleosides, oligonucleotides, antisense oligonucleotides, lipids, hormones, vitamins, and cells.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

The term "polymer" refers to a compound comprising eleven or more covalently connected repeating units. In certain embodiments, a polymer is naturally occurring. In certain embodiments, a polymer is synthetic (e.g., not naturally occurring). In certain embodiments, the $M_w$ of a polymer is between 1,000 and 2,000, between 2,000 and 10,000, between 10,000 and 30,000, between 30,000 and 100,000, between 100,000 and 300,000, between 300,000 and 1,000, 000, g/mol, inclusive. In certain embodiments, the $M_w$ of a polymer is between 2,000 and 1,000,000, g/mol, inclusive.

The term "tautomer" refers to each of two or more isomers of a compound that exist together in equilibrium, and are readily interchanged by migration of an atom or group within the molecule. "Tautomer" may also refer to an isomer of a compound that differs only in the position of the protons and electrons.

The term "average molecular weight" may encompass the number average molecular weight ($M_n$), weight average molecular weight ($M_w$), higher average molecular weight ($M_z$ or $M_z+1$), GPC/SEC(gel permeation chromatography/size-exclusion chromatography)-determined average molecular weight ($M_p$), and viscosity average molecular weight ($M_v$). Average molecular weight may also refer to average molecular weight as determined by gel permeation chromatography.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Unless expressly stated to the contrary, use of the term "a" is intended to include "at least one" or "one or more." For example, "a compound" is intended to include "at least one compound" or "one or more compounds."

DETAILED DESCRIPTION

The following paragraphs define in more detail the embodiments of the invention described herein. These embodiments are not meant to limit the invention or narrow the scope thereof, as it will be readily apparent to one of ordinary skill in the art that suitable modifications and adaptations may be made without departing from the scope of the invention, embodiments, or specific aspects described herein.

The present disclosure relates to polymers that are inherently difficult to degrade. The introduction of low levels of cleavable comonomer additives into existing vinyl polymerization processes facilitates the production of chemically deconstructable and recyclable variants with otherwise equivalent properties without requiring new monomer feedstocks, significantly raising costs, or altering manufacturing processes. Disclosed herein are polymer compositions that allow for chemical deconstruction of a polymer with a nucleophile. The polymer compositions disclosed herein can be used for cosmetic purposes and lead to easier removal than traditional cosmetic polymers, examples of which may also be found in U.S. patent application Nos. 63/308,497 and 63/308,492, incorporated herein by reference. An example reaction of the addition of a cleavable comonomer to a vinyl polymerization process and the destruction of the polymer with a nucleophile is illustrated in FIG. 1.

In one aspect, the present disclosure describes a polymer composition having first, second, and third monomer components. In some embodiments, the first monomer is of Formula (I) and tautomers and salts thereof.

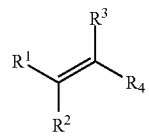

wherein $R^1$, $R^2$, and $R^3$ are each independently hydrogen, halogen, or substituted or unsubstituted alkyl. In certain embodiments, $R^1$ is H. In certain embodiments, $R^2$ is H. In certain embodiments, $R^3$ is H. In certain embodiments, $R^3$ is substituted or unsubstituted alkyl. In certain embodiments, $R^3$ is unsubstituted $C_1$-$C_6$ alkyl.

In certain embodiments, $R^4$ is halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^a$, —SCN, —SR$^a$—SSR$^a$, —N$_3$, —NO, —N(R$^a$)$_2$, —NO$_2$, —C(=O)R$^a$, —C(=O)OR$^a$, —C(=O)SR$^a$, —C(=O)N(R$^a$)$_2$, —C(=NR$^a$)R$^a$, —C(=NR$^a$)OR$^a$, —C(=NR$^a$)SR$^a$, —C(=NR$^a$)N(R$^a$)$_2$, —S(=O)R$^a$, —S(=O)OR$^a$, —S(=O)SR$^a$, —S(=O)N(R$^a$)$_2$, —S(=O)$_2$R$^a$, —S(=O)$_2$OR$^a$, —S(=O)$_2$SR$^a$, —S(=O)$_2$N(R$^a$)$_2$, —OC(=O)R$^a$, —OC(=O)OR$^a$, —OC(=O)SR$^a$, —OC(=O)N(R$^a$)$_2$, —OC(=NR$^a$)R$^a$, —OC(=NR$^a$)OR$^a$, OC(=NR$^a$)SR$^a$, —OC(=NR$^a$)N(R$^a$)$_2$, —OS(=O)R$^a$, —OS(=O)OR$^a$, —OS(=O)SR$^a$, —OS(=O)N(R$^a$)$_2$, —OS(=O)$_2$R$^a$, —OS(=O)$_2$OR$^a$, —OS(=O)$_2$SR$^a$, —OS(=O)$_2$N(R$^a$)$_2$, —ON(R$^a$)$_2$, —SC(=O)R$^a$, —SC(=O)OR$^a$, —SC(=O)SR$^a$, —SC(=O)N(R$^a$)$_2$, —SC(=NR$^a$)R$^a$, SC(=NR$^a$)OR$^a$, —SC(=NR$^a$)SR$^a$, —SC(=NR$^a$)N(R$^a$)$_2$, —NR$^a$C(=O)R$^a$—NR$^a$C(=O)OR$^a$, —NR$^a$C(=O)SR$^a$, —NR$^a$C(=O)N(R$^a$)$_2$, —NR$^a$C(=NR$^a$)R$^a$, —NR$^a$C(=Na)OR$^{aa}$, —NR$^a$C(=NR$^a$)SR$^a$, —NR$^a$C(=NR$^a$)N(R$^a$)$_2$, —NR$^a$S(=O)R$^a$, —NR$^a$S(=O)OR$^a$, —NR$^a$S(=O)SR$^a$—NR$^a$S(=O)N(R$^a$)$_2$, —NR$^a$S(=O)$_2$R$^a$—NR$^a$S(=O)$_2$OR$^a$, —NR$^a$S(=O)$_2$SR$^a$, —NR$^a$S(=O)$_2$N(R$^a$)$_2$, —Si(R$^a$)$_3$, —Si(R$^a$)$_2$OR$^a$, —Si(R$^a$)(OR$^a$)$_2$, —Si(OR$^a$)$_3$, —OSi(R$^a$)$_3$, —OSi(R$^a$)$_2$OR$^a$, —OSi(R$^a$)(OR$^a$)$_2$, or —OSi(OR$^a$)$_3$;

each instance of R$^a$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom. In certain embodiments, R$^4$ is —C(=O)OR$^a$. In certain embodiments, R$^4$ is —C(=O)N(R$^a$)$_2$, provided that at least one R$^a$ is not hydrogen. In certain embodiments, at least one R$^a$ is substituted or unsubstituted alkyl. In certain embodiments, at least one R$^a$ is substituted or unsubstituted alkyl. In certain embodiments, R$^4$ is substituted or unsubstituted phenyl. In certain embodiments, R$^4$ is unsubstituted phenyl.

In certain embodiments, none of R$^1$, R$^2$, R$^3$, R$^4$, R$^7$, R$^8$, and Ring B comprise one or more non-aromatic unsaturated CC bonds.

In certain embodiments, Formula I is of one of the following formulas:

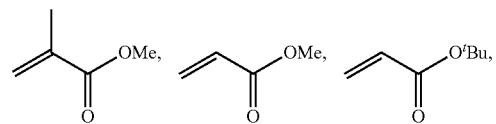

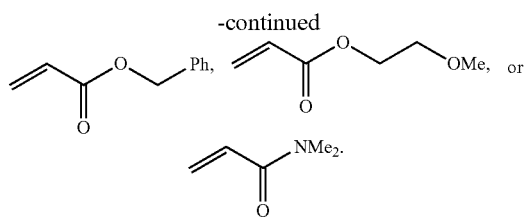

In certain embodiments, the second monomer is of the formula:

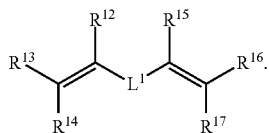

or a tautomer or salt thereof, wherein $R^{12}$, $R^{13}$, $R^{14}$, $R^{15}$, $R^{16}$, and $R^{17}$ are each independently hydrogen, halogen, or substituted or unsubstituted alkyl. In certain embodiments, $R^{12}$, $R^{13}$, $R^{14}$, $R^{15}$, $R^{16}$, and $R^{17}$ are each hydrogen.

In certain embodiments, $L^1$ is substituted or unsubstituted, $C_{1-1000}$ heteroalkylene, optionally wherein one or more backbone carbon atoms of the $C_{1-1000}$ heteroalkylene are independently replaced with substituted or unsubstituted arylene. In certain embodiments, $L^1$ is substituted or unsubstituted, $C_{10-100}$ heteroalkylene, optionally wherein one or more backbone carbon atoms of the $C_{1-1000}$ heteroalkylene are independently replaced with substituted or unsubstituted arylene. In certain embodiments, $L^1$ is substituted or unsubstituted, $C_{10-50}$ heteroalkylene, optionally wherein one or more backbone carbon atoms of the $C_{1-1000}$ heteroalkylene are independently replaced with substituted or unsubstituted phenylene.

In some embodiments, the third monomer is of Formula IV or tautomers or salts thereof:

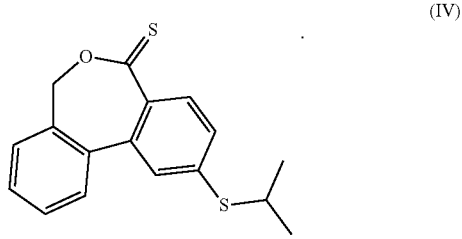 [SMILES: CC(C)Sc1ccc2c(c1)-c1ccccc1COC2=S]

(IV)

A person skilled in the art will appreciate that the first monomer may be a number of molecules capable of polymerization. In some embodiments, the first monomer is a polystyrene. In other embodiments, the first monomer is a methacrylate.

In some embodiments, the polymer composition includes various additives. For example, in some embodiments, the polymer composition includes a solvent. The solvent may include, but is not limited to, ethyl acetate, butyl acetate, propyl acetate, isopropyl acetate, or toluene. In certain embodiments, the polymer composition includes a cosmetically acceptable excipient. A person skilled in the art will appreciate that any number of excipients may be included in the composition, including but not limited to a thickener (i.e., stearalkonium hectorite), a coloring agent or pigment, a photoinitiator, a resin, a pigment dispersant, a UV stabilizer (i.e., benzophenone-1), a plasticizer, and a mica. In certain embodiments, the polymer composition includes more than one excipient.

For example, in some embodiments, the photoinitator may comprise, but is not limited to, sulfanyl ketone, sulfonyl azide, phosphinate, phosphine oxide, polymeric morpholinoketone, alpha amino ketone or iodonium hexafluorophosphate salt. In some embodiments, the plasticizer may comprise, but is not limited to, polyesters, resins, epoxies, methacrylic and vinyl copolymers, ethylene acetate, vinyl acetate copolymers, cellulose acetate, cellulose acetate butyrate, ethyl cellulose, and dimethicone. The resin may comprise, but is not limited to, nitrocellulose, polyurethane resins, alkyd resins, and polyvinyl resins.

In some embodiments, the pigment or a combination of pigments may comprise, but is not limited to, D & C Violet #2, D & C Green #5, D & C Red #6, D & C Red #7, D & C Red #17, D & C Red #21, D & C Red #22, D & C Red #27, D & C Red #28, D & C Red #30, D & C Red #31, D & C Red #33, D & C Red #34, D & C Red #36, D & C Red #40, FD & C Blue #1, D & C Yellow #5, D & C Yellow #7, D & C Yellow #8, D & C Yellow #10, D & C Yellow #11, FD & C Blue #1, FD & C Red #40, FD & C Red #4, FD & C Yellow #5, FD & C Yellow #6, D & C Black #2, D & C Orange #4, D & C Orange #5, D & C Orange #10, D & C Orange #11, cadmiums, titanium dioxide, barium, calcium and aluminum lakes, bismuth oxychlorides, talcs, carmine, chromates, iron oxides, metallic or mixed metallic oxides.

The first, second, and third monomer in the polymer composition may exist in a number of formulations having different relative proportions of the monomers to one another. In some embodiments, the first, second, and third monomer exist in about equal amounts in the polymer composition. In certain embodiments, the third monomer exists in a ratio of 1:4 to the first and second monomers. In some embodiments, the third monomer comprises 1-10 wt % of the polymer composition. In some embodiments, the third monomer comprises 0.5-5 wt % of the polymer composition. In some embodiments, the third monomer comprises 0.5-2 wt % of the polymer composition.

Figure 4:
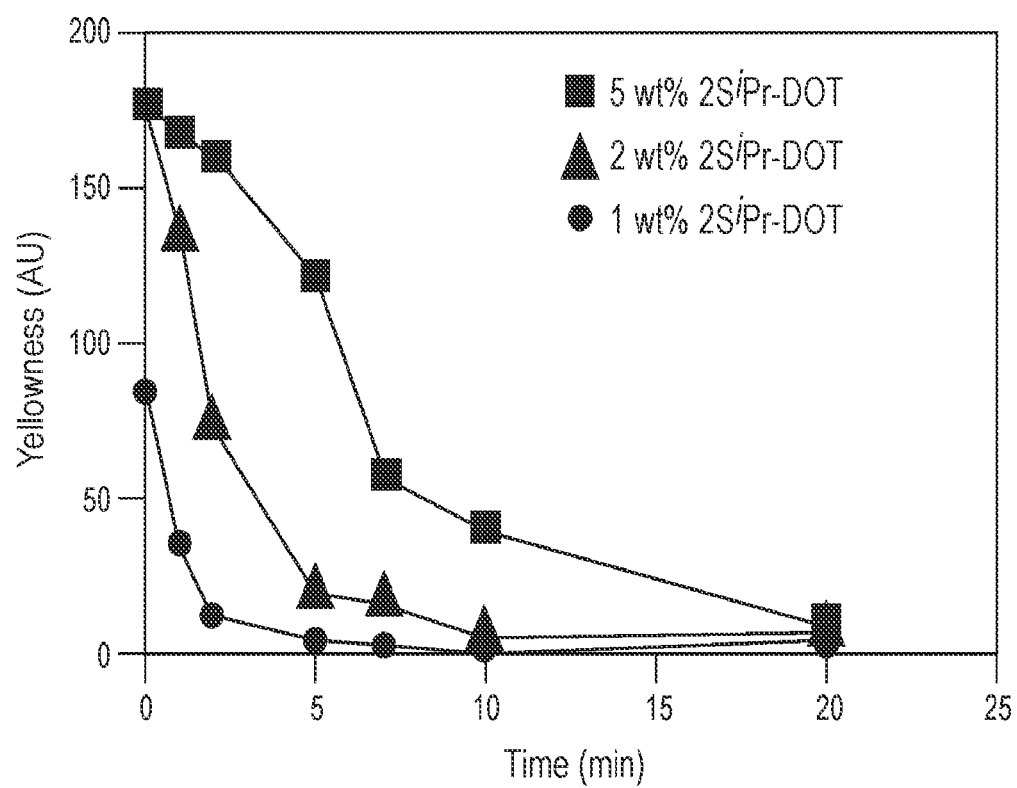
FIG. 4 shows a graph of the yellowness (AU) of a polymer matrix comprising various weight percentages of a monomer over time.

In some embodiments, the polymer composition is prepared by polymerizing the first, second, and third monomers. In certain embodiments, the third monomer is added subsequently to a mixture of at least the first and second monomers. When added to the polymer composition, the third monomer may contribute a visible absorbance that obscures the intended color of the polymer. Surprisingly, the 2SiPr-DOT compound does not contribute a permanent color as the visible absorbance disappears upon polymerization. In some embodiments, UV irradiation initiates the polymerization process. The disappearance of the visible absorbance can be measured by image analysis in ImageJ. FIG. 4 shows a graph depicting the disappearance of visible absorbance or "yellowness" in 2SiPr-DOT polymer compositions during exposure to UV irradiation overtime. As shown, the visible absorbance of polymer compositions with concentrations of 1, 2, and 5 wt % 2SiPr-DOT disappears after 20 minutes of UV irradiation. Compositions with lower concentrations show a disappearance of viable absorbance between about 5 and about 10 minutes of UV irradiation.

The polymer compositions may be utilized in a number of ways, one of which being in a gel nail polish composition. In select embodiments, the polymer composition is used to color a human's nails by applying the polymer composition to a nail bed. In certain embodiments, a consumer applies the polymer composition to a nail bed by coating a tool, i.e., a brush, in the polymer composition and then brushing the tool along the surface of the nail bed. In some embodiments, UV irradiation subsequently cures the polymer composition onto the nail bed.

Figure 3:
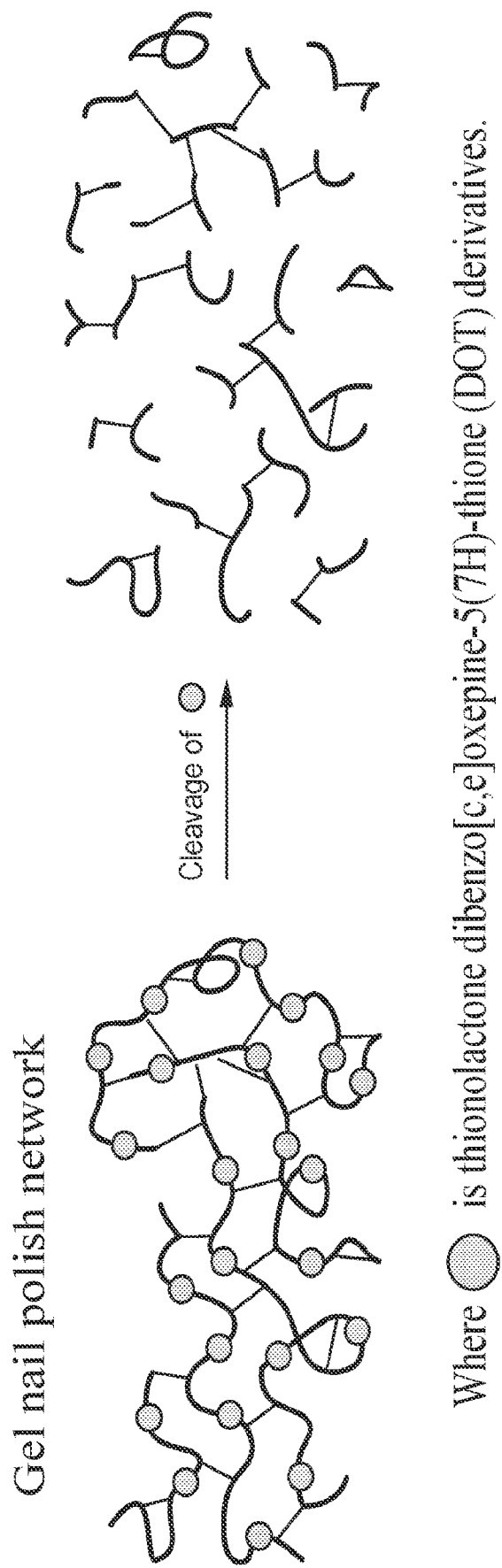
FIG. 3 depicts the degradation of a polymer matrix using an embodiment of the invention.

The addition of a cleavable monomer in the gel polish polymer creates a polymer network that is easily deconstructable with a removal solution such as the removal solutions disclosed herein. In some embodiments, the cleavable monomer can be thiolactone dibenzo[c,e]oxepine-5 (7H)-thione (DOT) or a derivative thereof as shown in FIG. 3.

In another aspect, a method of removing a polymer composition is described, where a removal solution comprising cysteine and an aqueous base is applied to a polymer composition. In some embodiments, the polymer composition comprises a first, second, and third monomer, the third monomer being of Formula III or a tautomer or salt thereof:

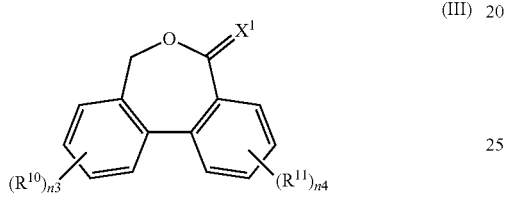

(III)

wherein $X^1$ is S or O;

each instance of $R^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —$OR^b$, —SCN, —$SR^b$, —$SSR^b$, —$N_3$, —NO, —$N(R^b)_2$, —$NO_2$, —C(=O)$R^b$, —C(=O)$OR^b$, —C(=O)$SR^b$, —C(=O)$N(R^b)_2$, —C(=$NR^b$)$R^b$, —C(=$NR^b$)$OR^b$, —C(=$NR^b$)$SR^b$, —C(=$NR^b$)$N(R^b)_2$, —S(=O)$R^b$, —S(=O)$OR^b$, —S(=O)$SR^b$, —S(=O)$N(R^b)_2$, —S(=O)$_2R^b$, —S(=O)$_2OR^b$, —S(=O)$_2SR^b$, —S(=O)$_2N(R^b)_2$, —OC(=O)$R^b$, —OC(=O)$OR^b$, —OC(=O)$SR^b$, —OC(=O)$N(R^b)_2$, —OC(=$NR^b$)$R^b$, —OC(=$NR^b$)$OR^b$, —OC(=$NR^b$)$SR^b$, —OC(=$NR^b$)$N(R)_2$, —OS(=O)$R^b$, —OS(=O)$OR^b$, —OS(=O)$SR^b$, —OS(=O)$N(R^b)_2$, —OS(=O)$_2R^b$, —OS(=O)$_2OR^b$, —OS(=O)$_2SR^b$, —OS(=O)$_2N(R^b)_2$, —ON($R^b)_2$, —SC(=O)$R^b$, —SC(=O)OR, —SC(=O)$SR^b$, —SC(=O)$N(R^b)_2$, —SC(=$NR^b$)$R^b$, —SC(=$NR^b$)$OR^b$, —SC(=$NR^b$)$SR^b$, —SC(=$NR^b$)$N(R^b)_2$, —$NR^bC$(=O)$R^b$, —$N^bC$(=O)$OR^b$, —$NR^bC$(=O)$SR^b$, —$NR^bC$(=O)$N(R^b)_2$, —$NR^bC$(=$NR^b$)$R^b$, —$NR^bC$(=$NR^b$)$OR^b$, —$NR^bC$(=$NR^b$)$SR^b$, —$NR^bC$(=$NR^b$)$N(R^b)_2$, —$NR^bS$(=O)$R^b$, —$NR^bS$(=O)$OR^b$, —$NR^bS$(=O)$SR^b$, —$NR^bS$(=O)$N(R^b)_2$, —$NR^bS$(=O)$_2R^b$, —$NR^bS$(=O)$_2OR^b$, —$NR^bS$(=O)$_2SR^b$, —$NR^bS$(=O)$_2N(R^b)_2$, —Si($R^b)_3$, —Si($R^b)_2OR^b$, —Si($R^b$)(OR$^b)_2$, —Si(OR$^b)_3$, —OSi($R^b)_3$, —OSi($R^b)_2OR^b$, —OSi($R^b$)(OR$^b)_2$, or —OSi(OR$^b)_3$;

each instance of $R^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —$OR^b$, —SCN, —$SR^b$, —$SSR^b$, —$N_3$, —NO, —$N(R^b)_2$, —$NO_2$, —C(=O)$R^b$, —C(=O)$OR^b$, —C(=O)$SR^b$, —C(=O)$N(R^b)_2$, —C(=$NR^b$)$R^b$, —C(=$NR^b$)$OR^b$, —C(=$NR^b$)$SR^b$, —C(=$NR^b$)$N(R^b)_2$, —S(=O)$R^b$, —S(=O)$OR^b$, —S(=O)$SR^b$, —S(=O)$N(R^b)_2$, —S(=O)$_2R^b$, —S(=O)$_2OR^b$, —S(=O)$_2SR^b$, —S(=O)$_2N(R^b)_2$, —OC(=O)$R^b$, —OC(=O)$OR^b$, —OC(=O)$SR^b$, —OC(=O)$N(R^b)_2$, —OC(=$NR^b$)$R^b$, —OC(=$NR^b$)$OR^b$, —OC(=$NR^b$)$SR^b$, —OC(=$NR^b$)$N(R^b)_2$, —OS(=O)$R^b$, —OS(=O)$OR^b$, —OS(=O)$SR^b$, —OS(=O)$N(R^b)_2$, —OS(=O)$_2R^b$, —OS(=O)$_2OR^b$, —OS(=O)$_2SR^b$, —OS(=O)$_2N(R^b)_2$, —ON($R^b)_2$, —SC(=O)$R^b$, —SC(=O)OR, —SC(=O)$SR^b$, —SC(=O)$N(R^b)_2$, —SC(=$NR^b$)$R^b$, —SC(=$NR^b$)$OR^b$, —SC(=$NR^b$)$SR^b$, —SC(=$NR^b$)$N(R^b)_2$, —$NR^bC$(=O)$R^b$, $NR^bC$(=O)$OR^b$, $NR^bC$(=O)$SR^b$, —$NR^bC$(=O)$N(R^b)_2$, —$NR^bC$(=$NR^b$)$R^b$, —$NR^bC$(=$NR^b$)$OR^b$, —$NR^bC$(=$NR^b$)$SR^b$, —$NR^bC$(=$NR^b$)$N(R^b)_2$, —$NR^bS$(=O)$R^b$, —$NR^bS$(=O)$OR^b$, —$NR^bS$(=O)$SR^b$, —$NR^bS$(=O)$N(R^b)_2$, —$NR^bS$(=O)$_2R^b$, —$NR^bS$(=O)$_2OR^b$, —$NR^bS$(=O)$_2SR^b$, —$NR^bS$(=O)$_2N(R^b)_2$, —Si($R^b)_3$, —Si($R^b)_2OR$, —Si($R^b$)(OR$^b)_2$, —Si(OR$^b)_3$, —OSi($R^b)_3$, —OSi($R^b)_2OR^b$, —OSi($R^b$)(OR$^b)_2$, or —OSi(OR$^b)_3$; and n3 is 0, 1, 2, 3, or 4, n4 is 0, 1, 2, 3, or 4, and at least one of n3 and n4 is 1, 2, 3, or 4; provided that no instance of $R^{10}$ and $R^{11}$ comprises one or more non-aromatic unsaturated CC bonds.

In exemplary embodiments, introduction of z removal solution having cysteine and an aqueous base cleaves the third monomer of the polymer composition thereby facilitating removal of the polymer composition. In some embodiments, the third monomer is of Formula IV or a tautomer or salt thereof:

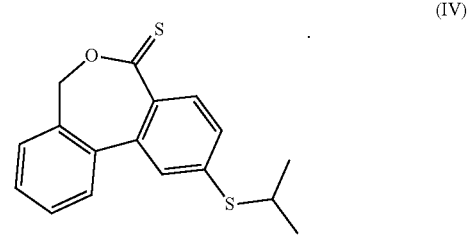 [SMILES: CC(C)Sc1ccc2c(c1)-c1ccccc1COC2=S]

(IV)

In other embodiments, the first monomer is of Formula I:

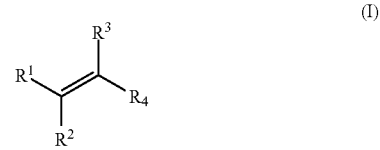

(I)

wherein $R^1$, $R^2$, and $R^3$ are each independently hydrogen, halogen, or substituted or unsubstituted alkyl;

$R^4$ is halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —$OR^a$, —SCN, —$SR^{aa}$, —$SSR^a$, —$N_3$, —NO, —$N(R^a)_2$, —$NO_2$, —C(=O)$R^a$, —C(=O)$OR^a$, —C(=O)$SR^a$, —C(=O)$N(R^a)_2$, —C(=$NR^a$)$R^a$, —C(=$NR^a$)$OR^a$, —C(=$NR^a$)$S^a$, —C(=$NR^a$)$N(R^a)_2$, —S(=O)$R^a$, —S(=O)$OR^a$, —S(=O)$SR^a$, —S(=O)$N(R^a)_2$, —S(=O)$_2R^a$, —S(=O)$_2OR^a$, —S(=O)$_2SR^a$, —S(=O)$_2N(R^a)_2$, —OC(=O)$R^a$, —OC(=O)$OR^a$, —OC(=O)$SR^a$, —OC(=O)$N(R^a)_2$, —OC(=NR$^a$)R$^a$, —OC(=NR$^a$)OR$^a$, —OC(=NR$^a$)SR$^a$, —OC(=NR$^a$)N(R$^a$)$_2$, —OS(=O)R$^a$, —OS(=O)OR$^b$, —OS(=O)SR$^a$, —OS(=O)N(R$^a$)$_2$, —OS(=O)$_2$R$^a$, —OS(=O)$_2$OR$^a$, —OS(=O)$_2$SR$^a$, —OS(=O)$_2$N(R$^a$)$_2$, —ON(R$^a$)$_2$, —SC(=O)R$^a$, —SC(=O)OR$^a$, —SC(=O)SR$^a$, —SC(=O)N(R$^a$)$_2$, —SC(=NR$^a$)R$^a$, —SC(=NR$^a$)OR$^a$, —SC(=NR$^a$)SR$^a$, —SC(=NR$^a$)N(R$^a$)$_2$, —NR$^a$C(=O)R$^a$, —NR$^a$C(=O)OR$^a$, —NR$^a$C(=O)SR$^a$, NR$^a$C(=O)N(R$^a$)$_2$, —NR$^a$C(=NR$^a$)R$^a$, —NR$^a$C(=NR$^a$)OR$^a$, —NR$^a$C(=NR$^a$)SR$^a$, —NR$^a$C(=NR$^a$)N(R$^a$)$_2$, —NR$^a$S(=O)R$^a$, —NR$^a$S(=O)OR$^a$, —NR$^a$S(=O)SR$^{aa}$, —NR$^a$S(=O)N(R$^a$)$_2$, —NR$^a$S(=O)$_2$R$^a$, —NR$^a$S(=O)$_2$OR$^a$, —NR$^a$S(=O)$_2$SR$^a$, —NR$^a$S(=O)$_2$N(R$^a$)$_2$, —Si(R$^a$)$_3$, —Si(R$^a$)$_2$OR$^a$, —Si(R$^a$)(OR$^a$)$_2$, —Si(OR$^a$)$_3$, —OSi(R$^a$)$_3$, —OSi(R$^a$)$_2$OR$^a$, —OSi(R$^a$)(OR$^a$)$_2$, or OSi(OR$^a$)$_3$;

each instance of R$^a$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom.

In certain embodiments, the method includes the step of exposing the polymer composition to the removal solution for a period of time. In some embodiments, the period of time is about 10 to 20 minutes. In other embodiments, the period of time is about 5 to 30 minutes. In other embodiments, the period of time is about 15 to 45 minutes. In some embodiments, the method further includes the step of removing the polymer composition from a surface. A person skilled in the art will appreciate that removal may be done in a variety of ways, including but not limited to sanding, peeling, scraping, wiping, or chipping the polymer composition off the surface. In exemplary embodiments, the surface is a nail bed.

In some embodiments, the removal solution is comprised of cysteine, an aqueous base, and at least one other ingredient. In certain embodiments, the removal solution additionally comprises one or more solvents, including but not limited to acetone, ethanol, water, saline, or phosphate-buffered saline. In some embodiments, the aqueous base is sodium hydroxide. In some embodiments, the aqueous base can be, but is not limited to, lithium hydroxide, potassium hydroxide, rubidium hydroxide, cesium hydroxide, calcium hydroxide, strontium hydroxide, or barium hydroxide. In exemplary embodiments, the removal solution contains at least 0.1 mM cysteine. In other embodiments, the concentration of cysteine is about 0.1 to about 0.5 mM. In other embodiments, the concentration of cysteine is about 0.1 to about 2 mM. In other embodiments, the concentration of the base is about 0.1 to about 1.0 mM in solution. In exemplary embodiments, the introduction of an aqueous base with cysteine improves the effectiveness of the cysteine nucleophile in degrading the polymer and thus requires significantly less nucleophile than prior methods.

In another aspect, the present disclosure describes a kit comprising a nail polish composition, a removal solution comprising cysteine and an aqueous base, and instructions for use. The nail polish composition comprises a first, second and third monomer, wherein the third monomer is of Formula III or a tautomer or salt thereof:

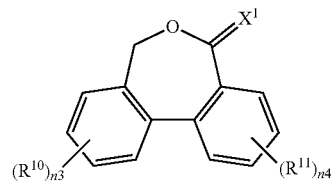

(III)

wherein X is S or O;

each instance of R$^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R)$_2$, —C(=NR$^b$)R$^b$, —C(=NR$^b$)OR$^b$, —C(=NR$^b$)SR$^b$, —C(=NR$^b$)N(R$^b$)$_2$, —S(=O)R$^b$, —S(=O)OR$^b$, —S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR$^b$, —OC(=O)N(R$^b$)$_2$, —OC(=NR$^b$)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR, —SC(=O)SR$^b$, —SC(=O)N(R$^b$)$_2$, —SC(=NR$^b$)R$^b$, —SC(=NR$^b$)OR$^b$, —SC(=NR$^b$)SR$^b$, —SC(=NR$^b$)N(R$^b$)$_2$, —NR$^b$C(=O)R$^b$, —NR$^b$C(=O)OR$^b$, —NR$^b$C(=O)SR$^b$, —NR$^b$C(=O)N(R$^b$)$_2$, —NR$^b$C(=NR$^b$)R$^b$, —N C(=NR$^b$)OC(R$^b$)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR, —OSi(R$^b$)(OR$^b$)$_2$, or —OSi(OR$^b$)$_3$;

each instance of R$^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR, —C(=O)SR$^b$, —C(=O)N(R$^b$)$_2$, —C(=NR$^b$)R$^b$, —C(=NR$^b$)OR, —C(=NR$^b$)SR$^b$, —C(=NR$^b$)N(R$^b$)$_2$, —S(=O)R$^b$, —S(=O)OR$^b$, —S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR, —OC(=O)SR$^b$, —OC(=O)N(R$^b$)$_2$, —OC(=NR$^b$)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR$^b$, —SC(=O)SR$^b$, —SC(=O)N(R$^b$)$_2$, —SC(=NR$^b$)R, —SC(=NR$^b$)OR$^b$, —SC(=NR$^b$)SR$^b$, —SC(=NR$^b$)N(R$^b$)$_2$, —NR$^b$C(=O)R$^b$, —NR$^b$C(=O)OR$^b$, —NR$^b$C(=O)SR$^b$, —NR$^b$C(=O)N(R$^b$)$_2$, —NR$^b$C(=NR$^b$)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S $(\!=\!\text{O})_2\text{N}(\text{R}^b)_2$, —Si($\text{R}^b$)$_3$, —Si($\text{R}^b$)$_2$O$\text{R}^b$, —Si($\text{R}^b$)(O$\text{R}^b$)$_2$, —Si(O$\text{R}^b$)$_3$, —OSi($\text{R}^b$)$_3$, —OSi($\text{R}^b$)$_2$O$\text{R}^b$, —OSi($\text{R}^b$)(O$\text{R}^b$)$_2$, or —OSi(O$\text{R}^b$)$_3$; and n3 is 0, 1, 2, 3, or 4, n4 is 0, 1, 2, 3, or 4, and at least one of n3 and n4 is 1, 2, 3, or 4; provided that no instance of $R^{10}$ and $R^{11}$ comprises one or more non-aromatic unsaturated CC bonds.

In some embodiments, the third monomer is Formula IV or a tautomer or salt thereof:

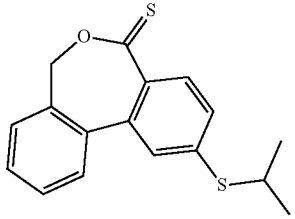

(IV)

In some embodiments, the nail polish composition comprises the first, second, and third monomer in about equal amounts in the polymer composition. In certain embodiments, the third monomer exists in a ratio of 1:4 to the first and second monomers.

In some embodiments, the removal solution is includes cysteine and an aqueous base. In some embodiments, the removal solution also includes and at least one other ingredient such as a buffering agent. In certain embodiments, the removal solution additionally includes an organic solvent selected from acetone and ethanol.

In some embodiments, the aqueous base is an alkaline hydroxide. In some embodiments, the aqueous base is sodium hydroxide. In some embodiments, the aqueous base is potassium hydroxide. In some embodiments, the aqueous base is lithium hydroxide. In some embodiments, the aqueous base is rubidium hydroxide. In some embodiments, the aqueous base is cesium hydroxide. In some embodiments, the removal solution has a pH of about 8-10. In certain embodiments, the removal solution has a pH of 9-9.5.

In some embodiments, the aqueous base is an alkaline earth hydroxide. In some embodiments, the aqueous base is magnesium hydroxide. In some embodiments, the aqueous base is calcium hydroxide. In some embodiments, the aqueous base is strontium hydroxide. In some embodiments, the aqueous base is barium hydroxide. In some embodiments, the aqueous base is sodium bicarbonate.

In certain embodiments, the removal solution has cysteine present in a concentration between about 0.1 to 2 mM. In some embodiments, the removal solution has cysteine present in a concentration between about 0.1 to 0.5 mM. In exemplary embodiments, the kit may further include a polymer composition container (i.e. a vial, ampule, bottle, syringe, dispenser, or other suitable container), and a removal solution container. In some embodiments, the kit further comprises a tool (i.e., a brush) for applying the polymer composition to a surface. In other embodiments, the kit further comprises a UV irradiation source.

The present disclosure enables to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. Furthermore, the foregoing Description is exemplary of the present invention and not limiting thereof. The scope of the invention is, therefore, set out in the appended claims.

Any composition disclosed herein may comprise, consist of, or consist essentially of any of the compounds or components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

EXAMPLES

General Considerations

Unless otherwise stated, all reactions were performed in dry solvents under an atmosphere of nitrogen, using either standard Schlenk techniques or a glovebox. "Room temperature", "RT", or "ambient temperature" refers to ~22° C. Reaction temperatures represent the oil bath temperature (with a fully submersed, stirred solution) unless otherwise stated.

Materials and Purification Methods

Reagent Solvent Sources and Purification

N,N-Dimethylformamide (DMF) used for polymer deconstruction was purchased Alfa Aesar (stock no: 43465, anhydrous, amine free, 99.9%), transferred to a Strauss flask containing 4 Å molecular sieves (5% by mass), and freed from 02 and residual amine by removal of 3-5% of the volume in vacuo. Cysteamine hydrochloride was recrystallized from absolute EtOH and stored in a desiccator. 2,2'-Azobis(2-methylpropionitrile)(AIBN) and 1,1'-azobis(cyanocyclohexane)(ACHN) were recrystallized from MeOH and absolute EtOH, respectively, and stored at ~2° C. Lawesson's reagent was purchased from Oakwood Chemical and used as received. All other reagents and solvents were purchased from commercial suppliers and used as received.

Chromatography

Column chromatography was carried out using Fischer Chemical 40-63 µm, 230-400 mesh silica gel. Preparatory thin layer chromatography (prep TLC) was carried out using Analtech Silica Gel GF UNIPLATES (1000 µm, 20×20 cm). For prep TLC, in a typical procedure, 35-50 mg of material was loaded onto one side of the plate and the solvent front was allowed to elute halfway up (i.e. 70-100 mg can be separated per plate).

Precipitation

Polymer precipitations carried out in this study were typically performed as follows. The crude polymer was dissolved in $CH_2Cl_2$ (~10 mL/g for low Mw samples and ~15 mL/g for high Mw samples) and this solution was added dropwise to a 10-fold excess of rapidly stirred MeOH (5-fold was sufficient in the case of decagram-scale purifications to avoid impractical volumes of solvent). The precipitate was collected on a medium porosity fritted funnel and the solid was quantitatively transferred to the frit with the aid of additional MeOH. The solid was allowed to dry in a stream of air on the frit for ~1 h, then this procedure was repeated the indicated number of times. To avoid excessive mechanical losses, especially on a small scale, $CH_2Cl_2$ was used to quantitatively recombine the precipitated solid before each subsequent precipitation. After the final precipitation, residual solvents were removed from the sample under high vacuum until the mass remained constant (>12 h at RT or 3 h at 50° C. were both found to be generally effective).

Analytical Methods

Nuclear Magnetic Resonance (NMR) Spectroscopy

Unless otherwise noted, NMR spectra were acquired at ambient temperature (~22° C.) at the MIT Department of Chemistry Instrumentation Facility using Bruker AVANCE III DRX 400 or Neo 500 spectrometers. Chemical shifts (δ) are given in ppm and referenced to residual solvent peaks for 1H NMR spectra (δ=7.26 ppm for chloroform-d, δ=7.16 for benzene-d6, δ=5.32 for dichloromethane-d2, and δ=2.09 for toluene-d8) and for 13C{1H} NMR spectra (δ=77.16 ppm for chloroform-d).

High Resolution Mass Spectrometry (HRMS)

HRMS measurements were obtained on a JEOL AccuTOF system at the MIT Department of Chemistry Instrumentation Facility.

Size Exclusion Chromatography (SEC)

Analytical gel permeation chromatography was performed on a Tosoh EcoSEC HLC-8320 with dual TSKgel SuperH3000 columns and an ethanol-stabilized chloroform mobile phase. Sample concentrations were ~1 mg/mL. Samples were filtered through 0.2 µm PTFE syringe filters before injection into the instrument. Molecular weight values were calculated according to linear polystyrene calibration standards. All SEC traces were referenced to a toluene internal standard.

Thermal Gravimetric Analysis (TGA)

TGA studies were performed on ~2-3 mg samples. Analyses were performed on a TGA/DSC 2 STAR System (Mettler-Toledo) equipped with a Gas Controller GC 200 Star System. Studies were performed under a constant stream of nitrogen gas at a temperature ramp of 20° C./min.

Differential Scanning Calorimetry (DSC)

DSC studies were performed on ~6-8 mg samples. Analyses were performed on a TGA/DSC 2 STAR System (Mettler-Toledo) equipped with a RCS1-3277 DSC cell and a DSC1-0107 cooling system. Each sample was sealed in an aluminum pan and subjected to three heating/cooling cycles from −20° C. to 200° C. at a rate of 10° C./min. The Tg values were recorded from the second heating ramp using the maximum absolute value of the derivative of heat flow with respect to temperature. DSC traces on the second and third heating cycles were identical for all samples reported herein.

Figure 5A:
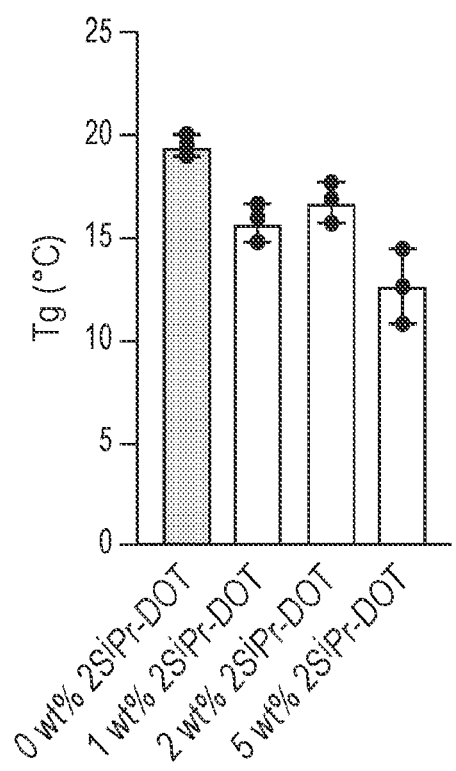
FIG. 5A shows the glass transition temperatures (Tg) of various polymer compositions comprising 0, 1, 2, and 5 wt % of 2S$^i$Pr-DOT.
Figure 6:
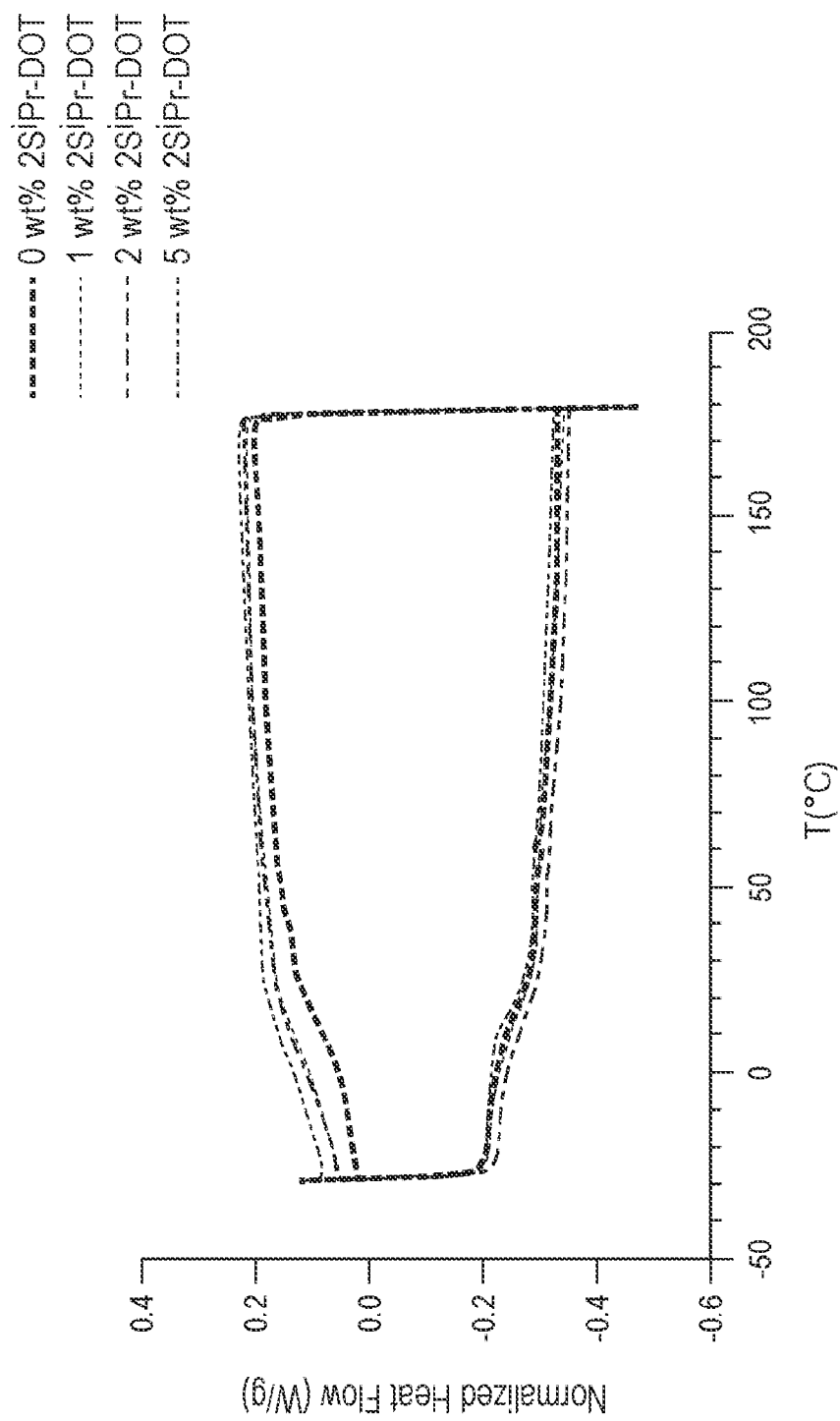
FIG. 6 depicts the normalized heat flow (W/g) of various polymer compositions comprising 0, 1, 2, and 5 wt % of 2S$^i$Pr-DOT over a temperature range (° C.).
Figure 7A:
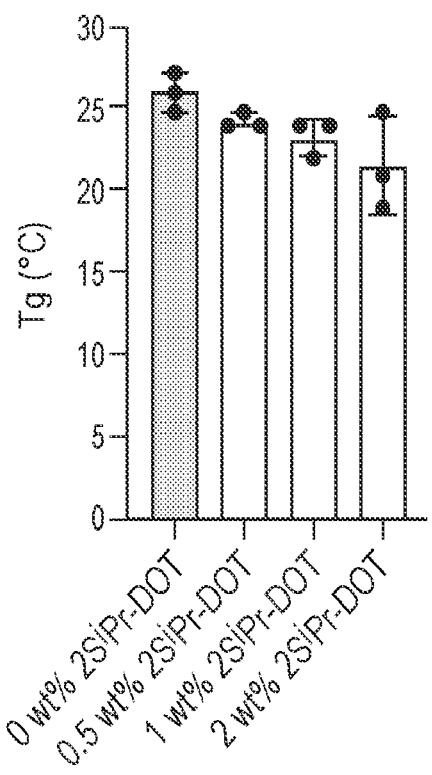
FIG. 7A shows the glass transition temperatures (Tg) of various polymer compositions comprising 0, 0.5, 1, and 2 wt % of 2S$^i$Pr-DOT.

Results of DSC studies on polymer composition comprising 0, 1, 2, and 5 wt % of 2SiPr-DOT are shown in FIGS. 5A and 6. Results of DSC studies on polymer composition comprising 0, 0.5, 1, and 2 wt % of 2SiPr-DOT are shown in FIG. 7A.

Dynamic Mechanical Analysis (DMA)

DMA was performed on a Discovery DMA 850 System (TA). Samples with dimensions ca. 2.5×1.0×12 mm (w×t×l), prepared as described below, were tested in tensile mode. Measurements were recorded at a frequency of 1 Hz and an amplitude of 0.1% strain from c.a. 40-180° C. at a heating rate of 3° C./min with a data sampling interval of 3 s/pt, using a 125% force tracking and 0.01N preload force. Data were collected using Trios software and exported to Microsoft Excel for analysis. Experiments were performed at the MIT Institute for Soldier Nanotechnologies. Reported modulus values in the main text are for measurements made at 40° C.

Figure 5B:
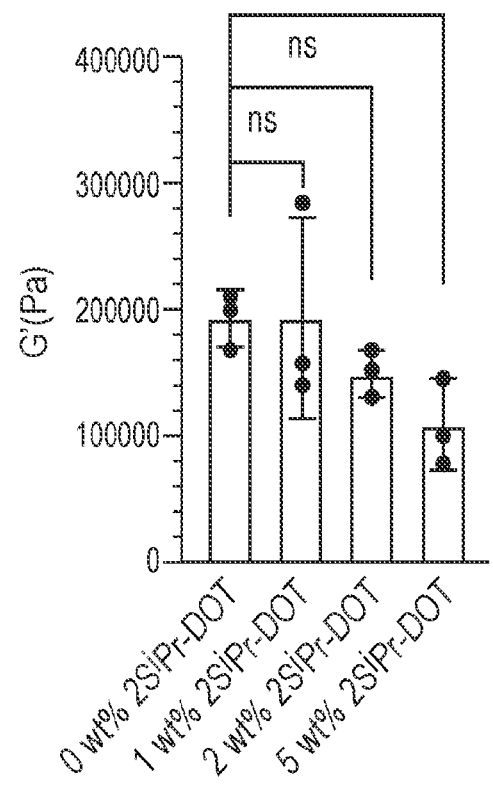
FIG. 5B shows the stiffness, measured as storage modulas (G'), of various polymer compositions comprising 0, 1, 2, and 5 wt % of 2S$^i$Pr-DOT.
Figure 7B:
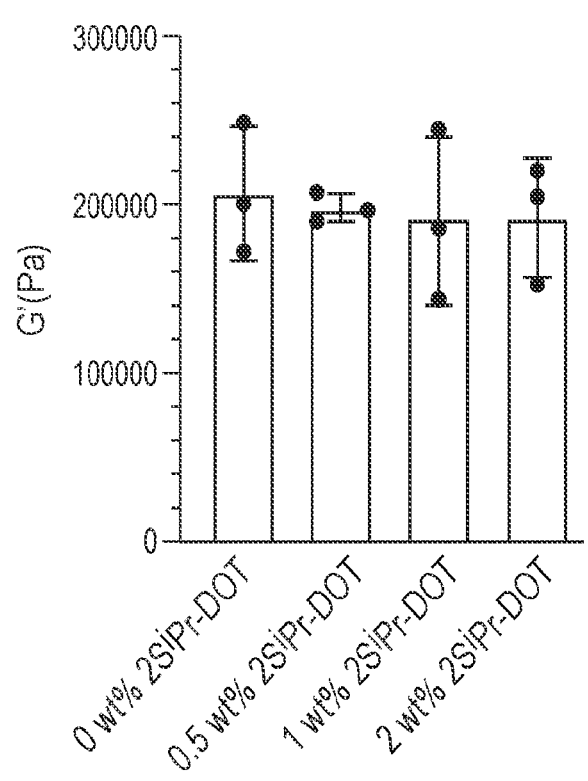
FIG. 7B shows the stiffness, measured as storage modulas (G'), of various polymer compositions comprising 0, 0.5, 1, and 2 wt % of 2S$^i$Pr-DOT.
Figure 8A:
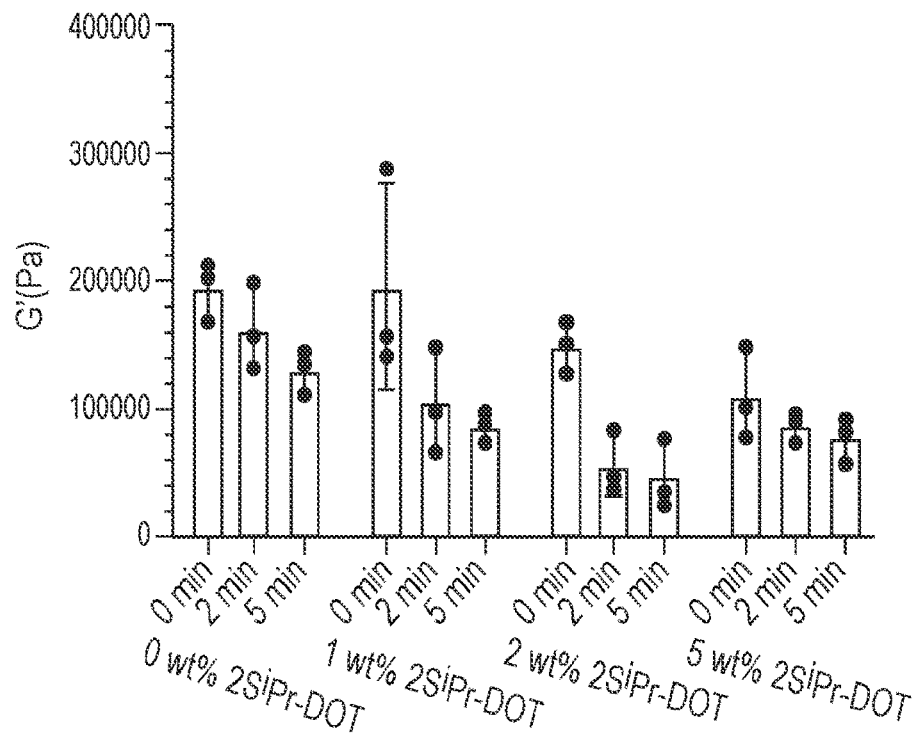
FIG. 8A shows the deconstruction, measured as storage modulas (G'), of gel nail polish comprising 0, 1, 2, and 5 wt % of 2S$^i$Pr-DOT when exposed to a 0.215 mM cysteine remover.
Figure 8B:
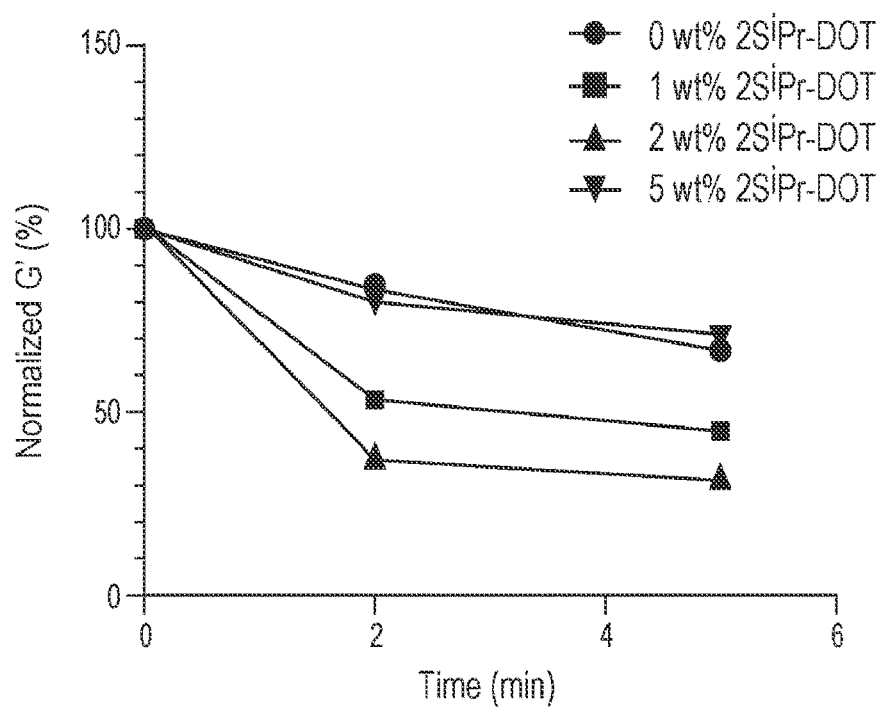
FIG. 8B shows a graph depicting the deconstruction of gel nail polish comprising 0, 1, 2, and 5 wt % of 2S$^i$Pr-DOT overtime when exposed to a 0.215 mM cysteine remover.
Figure 11:
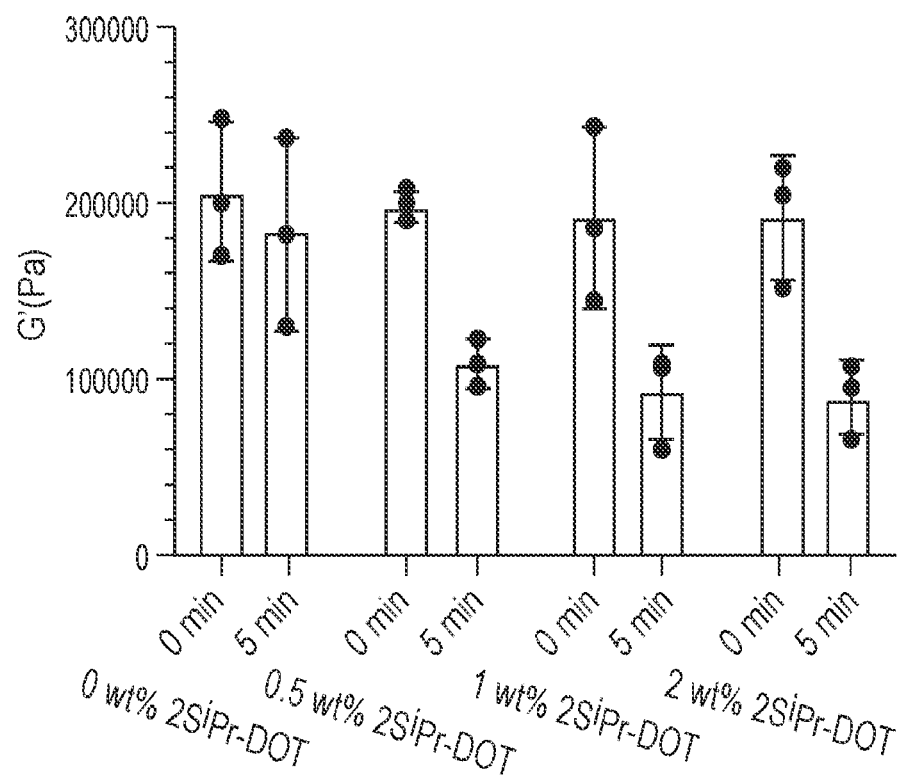
FIG. 11 shows the deconstruction, measured as storage modulas (G'), of gel nail polish comprising 0, 0.5, 1, and 2 wt % of 2S$^i$Pr-DOT when exposed to a 2 mM cysteine remover.

Results of DMA studies on polymer compositions comprising 0, 1, 2, and 5 wt % of 2SiPr-DOT are shown in FIGS. 5B and 8A-8B. Results of DMA studies on polymer compositions comprising 0, 0.5, 1, and 2 wt % of 2SiPr-DOT are shown in FIGS. 7B and 11.

Compression Molding for DMA Sample Preparation

Rectangular bars for DMA were prepared by compression molding of MeOH-precipitated samples. The solid was iteratively pressed into disks of 28 mm diameter and 1.5 mm thickness. First, eight circular samples were prepared by filling a die with PS and pressing at 4 tons pressure, 50° C. for 1 minute. Next, each of these samples was combined with another under identical conditions to produce four samples. This process was repeated once more to yield two disks, which were then pressed together under 4 tons of pressure at 130° C. for 10 minutes to yield a single transparent disk. Rectangular bars were cut from this disk and sanded to uniformity.

Evidence for Polymer Stability Under the Processing Conditions

The stability of each polymer (PS-hMW, dPS(2.5)-hMW, and rPS(2.5)-hMW) under the compression molding conditions described above was assessed by SEC analysis of pre- and post-processed material. The molecular weight distributions displayed no detectable changes in all cases.

Polymer Mass Loss and Swelling

Figure 9:
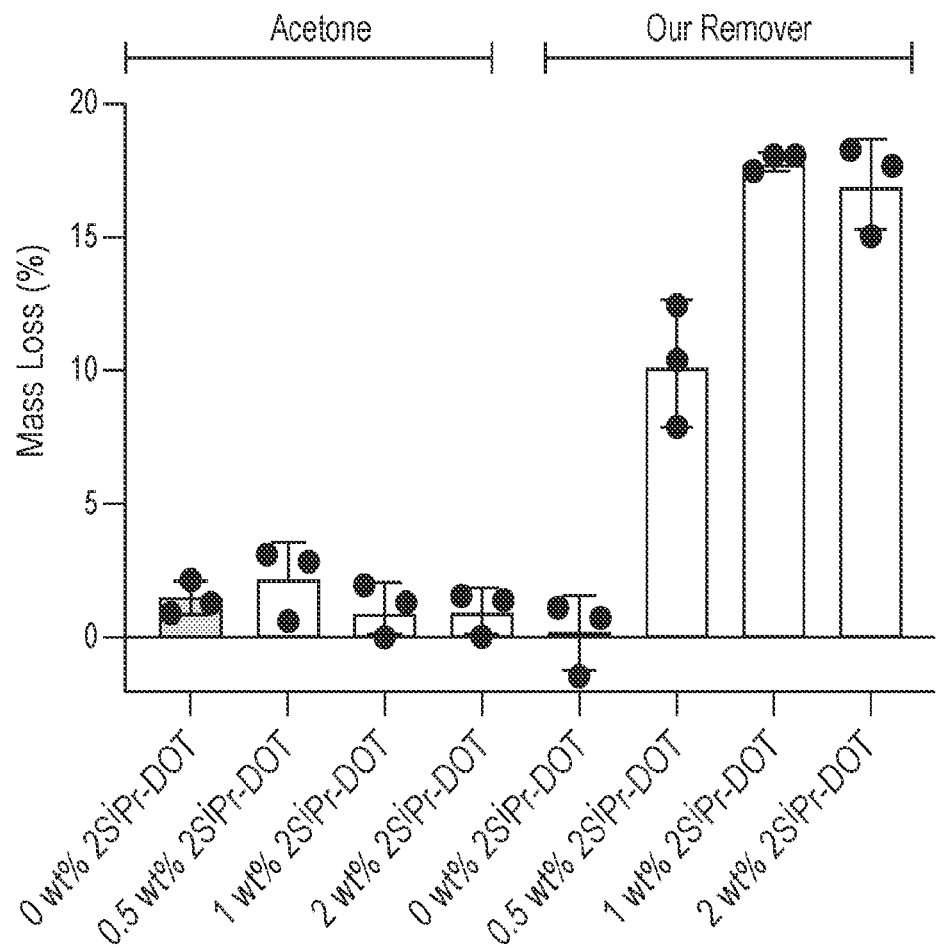
FIG. 9 shows the mass loss (%) of various polymer compositions comprising 0, 0.5, 1, and 2 wt % of 2S$^i$Pr-DOT when treated with acetone or a 2 mM cysteine remover solution.

Small samples of gel nail polish with 0, 0.5, 1, and 2 wt % of 2S$^i$Pr-DOT were cured under UV light for 10 minutes, and weighed. The cured samples were placed in 10 mL of a 2 mM cysteine remover solution or acetone as a control for 24 hours. The samples were then dried under vacuum overnight and weighed again. Mass % loss was calculated using the initial weight and the final weight after exposure to remover solution or control. As shown in FIG. 9, the mass loss % of samples exposed to a cysteine remover solution is greater than the mass loss % of the sample exposed to acetone only. The graph of FIG. 9 shows that samples of with higher wt % of 2S$^i$Pr-DOT had greater mass loss % when exposed to the cysteine remover solution while the sample containing 0 wt % 2S$^i$Pr-DOT shown negligible mass loss % when exposed to the cysteine remover solution indicating that the affect of the cysteine remover solution is present in nail polish samples containing 2S$^i$Pr-DOT.

Figure 10:
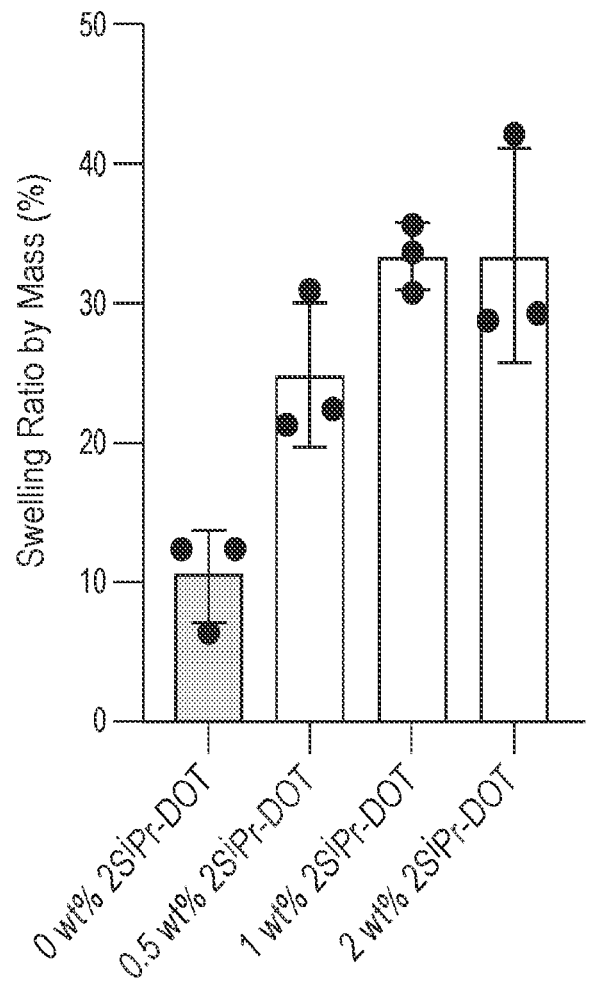
FIG. 10 shows the swelling ratio by mass (%) of various polymer compositions comprising 0, 0.5, 1, and 2 wt % of 2S$^i$Pr-DOT when treated with a 2 mM cysteine remover solution.

Small samples of gel nail polish with 0, 0.5, 1, and 2 wt % of 2S$^i$Pr-DOT were cured under UV light for 10 minutes. The cured samples were placed in 10 mL of a 2 mM cysteine remover solution for 1 hour and immediately weighed. The samples were then dried under vacuum for 6 hours weighed again. The difference between wet and dry sample weights was used to calculate the swelling %. The graph of FIG. 10 shows an increase in swelling ratio with an increase in wt % of 2S$^i$Pr-DOT in the gel nail polish.

Synthetic Details and Basic Structural Characterization

Naming Conventions

Monomers, oligomers, and polymers synthesized herein are named as shown in the scheme below. FX—Y-DOT represents the mol % of X—Y-DOT comonomer incorporated into the copolymer of styrene and X—Y-DOT. When X or Y=H, it is omitted from the name. For example, the DOT derivative with X=F and Y=H would be called F-DOT and the copolymer that incorporates 9.1% of this comonomer would be called F-dPS(9.1). The deconstruction product derived after treatment of this polymer with cysteamine gives a thiol at the α terminus and would thus be called thiol-F—OS(9.1). Finally, the recycled polymer obtained from oxidative polymerization of thiol-F—OS(9.1) would be called F-rPS(9.1). Lastly, for simplicity, molecular weights are broken up into two categories: low Mw (first part of the manuscript) and high Mw (second part of the manuscript). For the latter, "-hMW" is appended onto the name, e.g. the high Mw version of F-rPS(9.1) would be called F-rPS(9.1)-hMW.

General Route to Substituted DOTs

Figure 2:
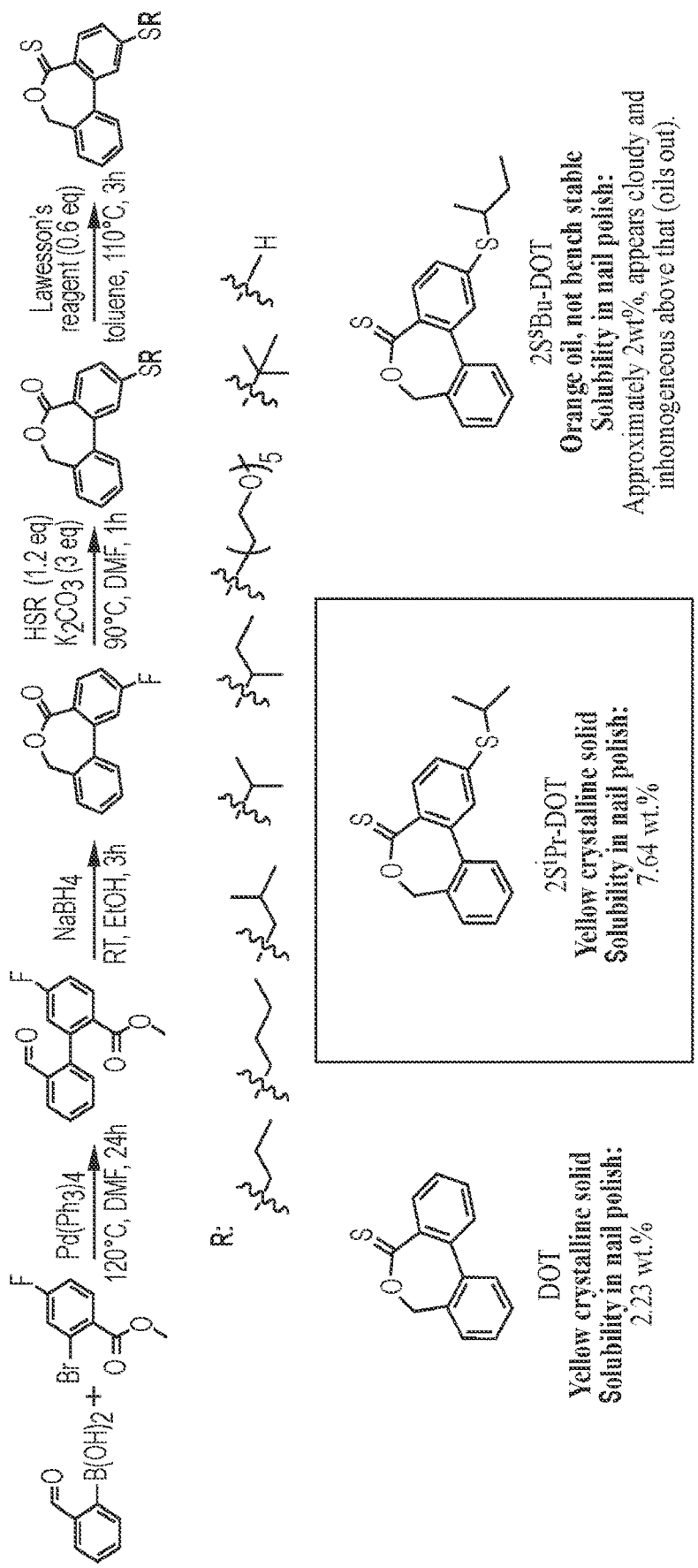
FIG. 2 shows a synthesis of 2S$^i$Pr-DOT. "2S$^i$Pr-DOT" refers to the thiolactone dibenzo[c,e]oxepine-5(7H)-thione that corresponds to a third monomer having an isopropyl thioester substituent.

Three different substituted DOT strategies were developed, all culminating in a thionation with Lawesson's reagent to produce the desired DOT derivative as shown in FIG. 2. These only differ in the details of the synthesis of the dibenzo[c,e]oxepin-5(7H)-one (DOO) precursor to the DOT derivative.

DOT

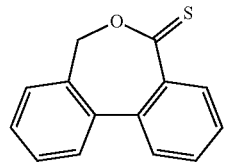 [SMILES: S=C1OCc2ccccc2-c2ccccc21]

IUPAC name: dibenzo[c,e]oxepine-5(7H)-thione.

Procedure: To improve scalability, the published procedure 6 was modified as follows: 1) increased concentration; 2) addition of a work-up step for decomposition of byproducts from Lawesson's reagent. An oven-dried, two-neck, 200 mL round-bottomed flask was equipped with a magnetic stirbar, reflux condenser, and N$_2$ inlet. The flask was charged with DOO (9.00 g, 42.8 mmol, 1.0 equiv) and Lawesson's reagent (10.4 g, 25.7 mmol, 0.60 equiv), the system was evacuated and backfilled with N$_2$, then anhydrous toluene (43 mL) was added. The stirred mixture was heated at 115° C. for 5 h under light N$_2$ flow, then volatile materials were removed via rotary evaporation at 60° C. The residue was dissolved in CH$_2$Cl$_2$ (50 mL), then mixture was diluted with MeOH(150 mL) and stirred vigorously for 12 h.* The suspension was concentrated to a total mass of ~20 g, diluted with MeOH(50 mL), filtered, and the solid was washed with MeOH(2×30 mL). The solid subjected to column chromatography (5-30% CH$_2$Cl$_2$ in hexanes), affording DOT (5.6 g, 58%) as a bright yellow, crystalline solid.*

*The step serves to decompose the byproducts from Lawesson's reagent into easily removable, MeOH-soluble species.

**The low solubility of DOT in this eluent necessitates dry loading. Here, we used 25-30 g of silica for this purpose and ~300 g total silica for the column.

***While not necessary, we have found it convenient to isolate this solid as follows (this also serves as a rapid, high recovery recrystallization). The product-containing fractions were concentrated to dryness, then the solid was dissolved in CH$_2$Cl$_2$ (50 mL). The solution was diluted with hexanes (300 mL), then the suspension was concentrated to a total mass of ~100 g and filtered. The solid was washed with hexanes (2×30 mL) and dried under high vacuum. Recovery: 5.3 g bright yellow crystalline solid.

Characterization: Basic characterization data ($^1$H and $^{13}$C NMR, and IR spectrum) matches that in the literature.

SPr-F-DOT

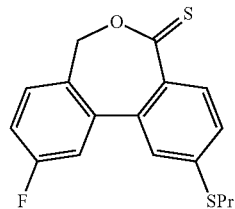

IUPAC Name: 10-fluoro-2-(propylthio)dibenzo[c,e]oxepine-5(7H)-thione.

Procedure: The following is a modified version of the procedure reported by Roth and coworkers for a similar compound. 6 The primary differences were with regard to concentration, reaction time, and equiv of Lawesson's reagent. A 15 mL Teflon-stoppered flask was loaded with SPr—F-DOO (0.700 g, 2.31 mmol, 1.0 equiv), Lawesson's reagent (0.562 g, 1.39 mmol, 0.60 equiv), and anhydrous toluene (2.3 mL). The flask was sealed, and the stirred mixture was heated at 110° C. for 3 h. The mixture was transferred to a round-bottomed flask with the aid of CH₂Cl₂, then solvents were removed via rotary evaporation. The residue was purified by column chromatography (5-25% EtOAc in hexanes) to afford SPr—F-DOT (0.426 g, 58%) as bright yellow/orange solid along with starting SPr—F-DOO (0.145 g, 21%) as a pale-yellow solid. The yield adjusted for recovered starting material was 73%.

Characterization: $^1$H NMR (chloroform-d, 400 MHz): δ=8.10 (d, J=8.4 Hz, 1H), 7.43 (dd, J=8.4, 5.5 Hz, 1H), 7.36-7.27 (m, 3H), 7.14 (td, J=8.3, 2.6 Hz, 1H), 5.24-5.04 (m, 2H), 3.02 (t, J=7.2 Hz, 2H), 1.77 (h, J=7.3 Hz, 2H), 1.08 (t, J=7.4 Hz, 3H); $^{19}$F{$^1$H} NMR (chloroform-d, 376 MHz): δ=−110.2; $^{13}$C{$^1$H} NMR (chloroform-d, 101 MHz): δ=214.92, 163.78 (d, J=249 Hz), 144.55, 141.04 (d, J=8.3 Hz), 135.58, 134.88, 133.95 (d, J=2.0 Hz), 130.85 (d, J=3.1 Hz), 130.55 (d, J=8.8 Hz), 126.42, 125.97, 115.92 (d, J=21.7 Hz), 115.38 (d, J=23.1 Hz), 72.87, 34.12, 22.27, 13.60; HRMS-DART-TOF (m/z): [M+H]⁺ calcd. For C₁₇H₁₆OFS₂, 319.0621; found, 319.0645.
SPr-DOT

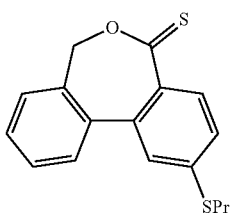

IUPAC Name: 2-(propylthio)dibenzo[c,e]oxepine-5(7H)-thione.

Procedure: This compound was prepared according to the procedure for SPr—F-DOT. The solid obtained from column chromatography was further purified as follows. The solid was dissolved in CH₂Cl₂ (1.0 mL) and hexanes (10 mL) was added, producing a crystalline precipitate. The suspension was cooled to −20° C. for 1 h and filtered. The solid was washed with hexanes (2×3 mL), affording SPr-DOT (635 mg, 60%) as yellow/orange crystalline solid.

Characterization: $^1$H NMR (chloroform-d, 400 MHz): δ=8.10 (d, J=8.4 Hz, 1H), 7.63 (d, J=7.7 Hz, 1H), 7.58-7.50 (m, 1H), 7.48-7.42 (m, 2H), 7.33 (d, J=1.9 Hz, 1H), 7.30 (dd, J=8.4, 1.9 Hz, 1H), 5.25-5.12 (m, 2H), 3.01 (t, J=7.2 Hz, 2H), 1.77 (h, J=7.3 Hz, 2H), 1.08 (t, J=7.4 Hz, 3H); $^{13}$C{H} NMR (chloroform-d, 101 MHz:) δ=215.47, 144.20, 138.83, 135.64, 135.11, 134.79, 134.74, 130.42, 129.09, 128.54, 128.44, 126.21, 125.98, 73.81, 34.13, 22.31, 13.61; HRMS-DART-TOF (m/z): [M+H]⁺ calcd. for C₁₇H₁₇OS₂, 301.0715; found, 301.0731.
F-DOT

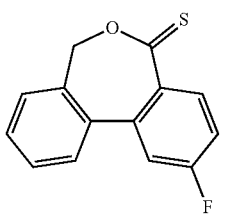 [SMILES: Fc1ccc2c(c1)-c1ccccc1COC2=S]

IUPAC Name: 2-fluorodibenzo[c,e]oxepine-5(7H)-thione.

Procedure: This compound was prepared according to the procedure for SPr—F-DOT. The solid obtained from column chromatography was further purified as follows. The solid was dissolved in CH₂Cl₂ (1.0 mL) and hexanes (10 mL) was added, producing an immediate crystalline precipitate. The suspension was cooled to −20° C. for 1 h and filtered. The solid was washed with hexanes (2×3 mL), affording F-DOT (220 mg, 41%) as a bright yellow crystalline solid.

Characterization: $^1$H NMR (chloroform-d, 400 MHz): δ=8.22 (dd, 1=8.8, 5.8 Hz, 1H), 7.63 (d, J=7.6 Hz, 1H), 7.60-7.52 (m, 1H), 7.52-7.44 (m, 2H), 7.21 (dd, J=9.5, 2.6 Hz, 1H), 7.15 (ddd, J=8.7, 7.7, 2.6 Hz, 1H), 5.44-4.92 (m, 2H); $^{19}$F{$^1$H} NMR (chloroform-d, 376 MHz): δ=−106.68; $^{13}$C{$^1$H} NMR: see spectrum below; HRMS-DART-TOF (m/z): [M+H]⁺ calcd. for C₁₄H₁₀FOS, 245.0431; found, 245.0423.
F₂-DOT

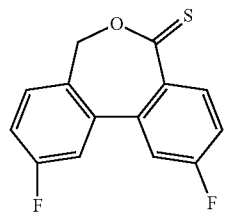 [SMILES: Fc1ccc2c(c1)-c1cc(F)ccc1C(=S)OC2]

IUPAC Name: 2,10-difluorodibenzo[c,e]oxepine-5(7H)-thione.

Procedure: This compound was prepared according to the procedure for SPr—F-DOT. The yellow solid (224 mg) obtained from column chromatography had ~2% impurity and was further purified as follows. The solid was dissolved in CH₂Cl₂ (1.0 mL) and hexanes (10 mL) was added, producing an immediate crystalline precipitate. The suspension was cooled to −20° C. for 1 h and filtered. The solid was washed with cold hexanes (2×3 mL), affording F₂-DOT (203 mg, 38%) as a bright yellow powder.

Characterization: $^1$H NMR (chloroform-d, 400 MHz): δ=8.22 (dd, J=9.6, 5.7 Hz, 1H), 7.46 (dd, J=8.4, 5.4 Hz, 1H), 7.34 (dd, J=9.2, 2.6 Hz, 1H), 7.23-7.12 (m, 3H), 5.30-5.02 (m, 2H); $^{19}$F NMR (chloroform-d, 376 MHz): δ=−106.28 (td, J=8.4, 5.6 Hz), −109.74 (td, J=8.8, 5.5 Hz); $^{13}$C{$^1$H} NMR (chloroform-d, 101 MHz): δ=214.05, 164.67 (d, J=255.4 Hz), 163.83 (d, J=249.8 Hz), 140.34 (dd, J=8.4, 1.7 Hz), 137.34 (d, J=9.1 Hz), 136.10 (dd, J=8.4, 2.1 Hz), 135.65 (d, J=3.2 Hz), 130.77 (d, J=8.9 Hz), 130.68 (d, J=3.0 Hz), 116.45 (d, J=11.0 Hz), 116.24 (d, J=10.9 Hz), 115.51 (d, J=23.2 Hz), 115.02 (d, J=23.0 Hz), 72.90; HRMS-DART-TOF (m/z): [M+H]⁺ calcd. for C₁₄H₉F₂OS, 263.0337; found, 263.0321.
OMe₂-DOT

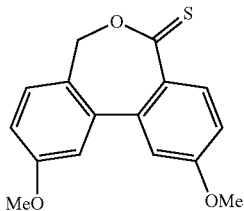 [SMILES: COc1ccc2c(c1)-c1cc(OC)ccc1C(=S)OC2]

IUPAC name: 2,10-dimethoxydibenzo[c,e]oxepine-5(7H)-thione.

Procedure: This compound was prepared according to the procedure for SPr—F-DOT. The crude mixture was purified by column chromatography (35-65% CH₂C₁₂ in hexanes) followed by precipitation of the desired product from a concentrated CH₂Cl₂ solution (~1 mL) with hexanes (5 mL). The isolated yield of OMe₂-DOT, a bright yellow solid, was 75 mg (14%).

Characterization: $^1$H NMR (chloroform-d, 400 MHz): δ=8.22-8.15 (m, 1H), 7.36 (d, J=8.3 Hz, 1H), 7.14 (d, J=2.6 Hz, 1H), 7.01-6.93 (m, 3H), 5.19-5.06 (m, 2H), 3.92 (s, 3H), 3.88 (s, 3H); $^{13}$C NMR (chloroform-d, 101 MHz): δ=215.89, 162.58, 161.03, 140.54, 136.99, 136.85, 132.33, 129.91, 127.41, 114.21, 114.14, 114.03, 113.24, 73.35, 55.81, 55.69; HRMS-DART-TOF (m/z): [M+H]$^+$ calcd. for C$_{16}$H$_{15}$O$_3$S, 287.0736; found, 287.0753.
DOO

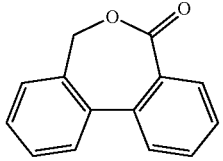 [SMILES: O=C1OCc2ccccc2-c2ccccc21]

IUPAC Name: dibenzo[c,e]oxepin-5(7H)-one.

Procedure: This compound was prepared by a slightly modified literature procedure (Brandmeier, V.; Feigel, M. A Macrocycle Containing Two Biphenyl and Two Alanine Subunits, Synthesis and Conformation in Solution. Tetrahedron 1989, 45 (5), 1365-1376). Yield: 21 g (86%).

Characterization: $^1$H and $^{13}$C NMR data matches that in the literature.[4]

F$_2$-DOO

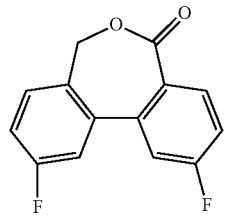 [SMILES: O=C1OCc2ccc(F)cc2-c2cc(F)ccc21]

IUPAC Name: 2,10-difluorodibenzo[c,e]oxepin-5(7H)-one.

Procedure: The following is an adaptation of the methodology developed by Miyagawa and Akiyama.[5] The primary modifications were with regard to concentration, workup, and purification. An oven-dried, 500 mL Schlenk flask was charged with 2-bromo-4-fluorobenzaldehyde (10.0 g, 49.3 mmol, 1.0 equiv), activated Zn powder (5.16 g, 78.9 mmol, 1.6 equiv), tetrabutylammonium iodide (36.4 g, 98.6 mmol, 2.0 equiv), and Ni(PPh$_3$)$_2$Cl$_2$ (1.62 g, 2.47 mmol, 0.05 equiv), then the flask was sealed with a rubber septum and deoxygenated with three vacuum/N$_2$ cycles. Anhydrous, N$_2$-sparged o-xylene (150 mL) was added via cannula, then the stirred mixture was heated to 135° C. (internal temperature). The rubber septum was exchanged for a ground-glass stopper and the stirred mixture was heated at 135° C. for 18 h. The hot, biphasic mixture was then transferred to a separatory funnel and the top, transparent layer (o-xylene) was set aside. The dark brown and viscous bottom layer (primarily tetrabutylammonium iodide) was extracted with toluene (50 mL). The combined o-xylene/toluene layers were filtered through a plug of silica gel (~20 g), the plug was flushed with CH$_2$Cl$_2$ (250 mL), and the filtrate was concentrated via rotary evaporation at RT followed by 70-80° C. The residue was dissolved in the minimal amount of boiling CH$_2$Cl$_2$ (15-20 mL), the solution was diluted with MeOH(150 mL), then the volume of the resulting mixture was reduced to ~50 mL via rotary evaporation. The precipitate was collected on a fritted funnel, washed with MeOH (3×20 mL), and dried under high vacuum to afford F$_2$-DOO (2.80 g, 46%) as an off-white solid.

Characterization: $^1$H NMR (chloroform-d, 400 MHz): δ=8.04 (dd, J=8.6, 5.8 Hz, 1H), 7.47 (dd, J=8.4, 5.5 Hz, 1H), 7.33 (dd, J=9.3, 2.6 Hz, 1H), 7.30-7.22 (m, 2H), 7.16 (td, J=8.3, 2.6 Hz, 1H), 5.00 (d, J=4.5 Hz, 2H); $^{19}$F{$^1$H} NMR (chloroform-d, 376 MHz): δ=−105.3, −110.1; $^{13}$C{$^1$H} NMR: see spectrum below; HRMS-DART-TOF (m/z): [M+H]$^+$ calcd. for C$_{14}$H$_9$O$_2$F$_2$, 247.0565; found, 247.0584.

F-DOO

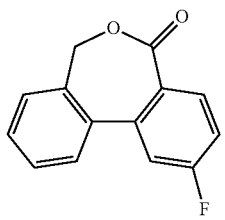 [SMILES: O=C1OCc2ccccc2-c2cc(F)ccc21]

IUPAC Name: 2-fluorodibenzo[c,e]oxepin-5(7H)-one.

Procedure: A 100 mL Schlenk flask was charged with methyl 2-bromo-4-fluorobenzoate (10.0 g, 42.9 mmol, 1.0 equiv), 2-formylphenylboronic acid (8.36 g, 55.8 mmol, 1.3 equiv), powdered anhydrous K$_3$PO$_4$ (11.8 g, 55.8 mmol, 1.3 equiv), and Pd(PPh3)$_4$ (0.50 g, 0.43 mmol, 0.01 equiv). The flask was sealed with a rubber septum and deoxygenated with three vacuum/N$_2$ cycles. Anhydrous, N$_2$-sparged DMF (43 mL) was added via syringe, then the stirred mixture was heated at 120° C. (oil bath temperature) under light N$_2$ flow for 24 h.* The mixture was partitioned between EtOAc (200 mL) and water (200 mL), then the organic layer was washed with water (200 mL) and saturated aqueous NaCl (200 mL), dried with MgSO$_4$, filtered into a 500 mL round-bottomed flask, and concentrated via rotary evaporation. Residual volatile materials were removed under high vacuum (~1 h), affording 11.4 g of a golden yellow oil. To the flask was then added a magnetic stirbar and absolute EtOH (200 mL). The resulting homogeneous solution was cooled to ~2° C. with an ice/water bath, then NaBH$_4$ (3.16 g, 83.6 mmol, 2 equiv) was added portionwise over 5-10 min, such that the temperature did not rise above 10° C. At the end of addition, the cold bath was removed, and the mixture was allowed to warm to RT and stirred for a further 2 h. The reaction was quenched by the careful addition water (300 mL), then the precipitate was collected by filtration and washed with water (3×50 mL). The resulting brown solid was dissolved in CH$_2$Cl$_2$ (125 mL), the solution was treated with MgSO$_4$, then the mixture was filtered through a plug of silica gel (20 g). The plug was eluted with CH$_2$Cl$_2$ until TLC indicated complete elution of the desired compound. Solvents were removed via rotary evaporation, then the resulting solid was further purified as follows. The crude solid was suspended in MeOH(75 mL), then the stirred suspension was brought to a boil for ~3 min. The mixture was allowed to cool to RT, then the solid was collected by filtration, washed with MeOH(2×30 mL), and dried under high vacuum. This afforded F-DOO (5.20 g, 53%) as a crystalline white solid.

Notes: *Analysis of aliquots after 1 h, 3 h, and 24 h by $^1$H NMR spectroscopy indicated that starting material conversions were 76%, 85%, and 100%, respectively.

Characterization: $^1$H NMR (chloroform-d, 400 MHz): δ=8.05 (dd, J=8.7, 5.9 Hz, 1H), 7.65 (d, J=7.7 Hz, 1H), 7.61-7.55 (m, 1H), 7.53-7.46 (m, 2H), 7.33 (dd, J=9.7, 2.6 Hz, 1H), 7.27-7.21 (m, 1H), 5.20-4.88 (m, 2H); $^{19}$F{$^1$H} NMR (chloroform-d, 376 MHz): δ=−105.85; $^{13}$C{$^1$H} NMR: see spectrum below. $^1$H NMR data is consistent with that reported in the literature.[6]

SPr—F-DOO

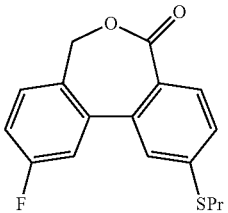

IUPAC Name: 10-fluoro-2-(propylthio)dibenzo[c,e]oxepin-5(7H)-one.

Procedure: A 100 mL Teflon-stoppered flask was loaded with $F_2$-DOO (1.40 g, 5.69 mmol, 1.0 equiv), $K_2CO_3$ (2.36 g, 17.1 mmol, 3.0 equiv), and anhydrous DMF (21 mL). The flask was crudely deoxygenated with three rapid vacuum/$N_2$ cycles (~15 seconds each), then 1-propanethiol (0.477 g, 6.26 mmol, 1.10 equiv) was added via syringe. The flask was sealed, and the vigorously stirred mixture was heated at 90° C. for 1 h. The mixture was cooled to RT, diluted with EtOAc (100 mL), washed with water (2×100 mL) and saturated aqueous NaCl (100 mL), dried with $MgSO_4$, and filtered. Solvents were removed from the filtrate via rotary evaporation, then the residue was purified by column chromatography (50-100% $CH_2Cl_2$ in hexanes) to afford SPr—F-DOO (1.41 g, 82%) as a white solid.

Characterization: $^1H$ NMR (chloroform-d, 400 MHz): δ=7.93-7.88 (m, 1H), 7.44 (dd, J=8.4, 5.5 Hz, 1H), 7.42-7.37 (m, 2H), 7.33 (dd, J=9.5, 2.6 Hz, 1H), 7.13 (td, J=8.3, 2.6 Hz, 1H), 5.09-4.89 (m, 2H), 3.03 (t, J=7.3 Hz, 2H), 1.78 (sext, J=7.3 Hz, 2H), 1.09 (t, J=7.3 Hz, 3H); $^{19}F\{^1H\}$ NMR (chloroform-d, 376 MHz): δ=−110.6; $^{13}C\{^1H\}$ NMR (chloroform-d, 101 MHz): δ=169.76, 163.72 (d, J=249 Hz), 144.83, 140.98 (d, J=8.1 Hz), 136.71 (d, J=2.2 Hz), 132.75, 131.19 (d, J=3.1 Hz), 130.70 (d, J=8.8 Hz), 127.03, 126.86, 126.39, 115.78 (d, J=22.3 Hz), 115.54 (d, J=23.0 Hz), 68.35, 34.18, 22.26, 13.61; HRMS-DART-TOF (m/z): [M+H]$^+$ calcd. for $C_{17}H_{16}O_2FS$, 303.0850; found, 303.0867.

SPr-DOO

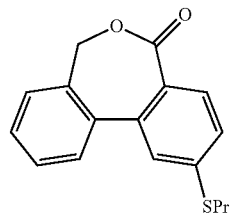

IUPAC Name: 2-(propylthio)dibenzo[c,e]oxepin-5(7H)-one.

Procedure: This compound was prepared according to the procedure for SPr—F-DOO, except 1.2 equiv of 1-propanethiol was used and 100% $CH_2Cl_2$ was used for column chromatography. The yield of SPr-DOO, a white solid, was 2.02 g (81%).

Characterization: $^1H$ NMR (chloroform-d, 400 MHz): δ=7.92 (d, J=8.3 Hz, 1H), 7.68-7.62 (m, 1H), 7.56 (ddd, J=7.8, 6.3, 2.5 Hz, 1H), 7.52-7.41 (m, 3H), 7.39 (dd, J=8.3, 1.9 Hz, 1H), 5.18-4.88 (m, 2H), 3.04 (t, J=7.2 Hz, 2H), 1.79 (sext, J=7.3 Hz, 2H), 1.10 (t, J=7.4 Hz, 3H); $^{13}C$ NMR (chloroform-d, 101 MHz): δ=170.11, 144.39, 138.76, 137.81, 135.08, 132.59, 130.27, 129.00, 128.72, 128.59, 127.06, 126.60, 126.41, 69.23, 34.20, 22.31, 13.61; HRMS-DART-TOF (m/z): [M+H]$^+$ calcd. for $C_{17}H_{17}O_2S$, 285.0944; found, 285.0951.

OMe$_2$-DOO

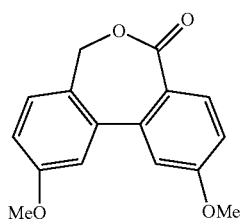 [SMILES: COc1ccc2c(c1)-c1cc(OC)ccc1C(=O)OC2]

IUPAC Name: 2,10-dimethoxydibenzo[c,e]oxepin-5(7H)-one.

Procedure: This compound was prepared according to the procedure for $F_2$-DOO, except the combined o-xylene/toluene extracts were concentrated via rotary evaporation at 70-80° C. and purified by column chromatography (50-100% $CH_2Cl_2$ in hexanes) to afford OMe$_2$-DOO as a white solid (0.77 g, 25%). Characterization: The $^1H$ NMR spectrum matches that presented in the literature.[7]

2S$^i$Pr-DOT

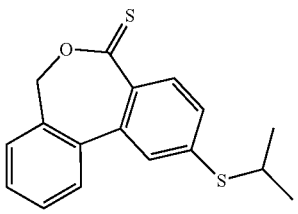 [SMILES: CC(C)Sc1ccc2c(c1)-c1ccccc1COC2=S]

IUPAC Name: 2-(isopropylthio)dibenzo[c,e]oxepine-5(7H)-thione.

Procedure: Synthesis of 2SiPrDOO. A 100 mL Teflon-stoppered flask was loaded with 2FDOO (1.40 g, 5.69 mmol, 1.0 equiv), $K_2CO_3$ (2.36 g, 17.1 mmol, 3.0 equiv), and anhydrous DMF (21 mL). The flask was crudely deoxygenated with three rapid vacuum/$N_2$ cycles (~15 seconds each), then 2-propanethiol (0.477 g, 6.26 mmol, 1.10 equiv) was added via syringe. The flask was sealed, and the vigorously stirred mixture was heated at 90° C. for 24 h. The mixture was cooled to RT, diluted with EtOAc (100 mL), washed with water (2×100 mL) and saturated aqueous NaCl (100 mL), dried with $MgSO_4$, and filtered. Solvents were removed from the filtrate via rotary evaporation, then the residue was purified by column chromatography (50-100% $CH_2Cl_2$ in hexanes) to afford 2SiPrDOO (1.41 g, 82%) as a white solid.

Synthesis of 2SiPrDOT. A 15 mL Teflon-stoppered flask was loaded with 2SiPrDOO (0.700 g, 2.31 mmol, 1.0 equiv), Lawesson's reagent (0.562 g, 1.39 mmol, 0.60 equiv), and anhydrous toluene (2.3 mL). The flask was sealed, and the stirred mixture was heated at 110° C. for 3 h. The mixture was transferred to a round-bottomed flask with the aid of $CH_2C_{12}$, then solvents were removed via rotary evaporation. The residue was purified by column chromatography (5-25% EtOAc in hexanes) to afford the cleavable comonomer 2SiPrDOT (0.426 g, 58%) as bright yellow/orange solid along with starting 2SiPrDOO (0.145 g, 21%) as a pale-yellow solid. The yield adjusted for recovered starting material was 73%.

Solubility Study

The solubility of various DOT derivatives in nail polish was observed by generating a supersaturated solution of the compounds in nail polish (clear topcoat). The supersaturated solution was filtered through a 0.25 μm PTFE syringe filter, and a known mass of an internal NMR standard (bis-1,4-trimethylsilylbenzene) was added. The amount of the compound that was dissolved in the nail polish was then determined by quantitative $^1H$ NMR. The solubility was taken as the amount of the weight fraction of the compound dissolved in nail polish in a supersaturated solution. As shown in FIG. 2 and the table below, 2S$^i$Pr-DOT shows superior solubility in nail polish over DOT or 2S$^s$Bu-DOT.

DOT Derivatives in Nail Polish

| Structure | Solubility (wt % in polish) | Notes |
|---|---|---|
| 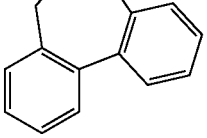<br>DOT | 2.23 | Yellow crystalline solid |
| 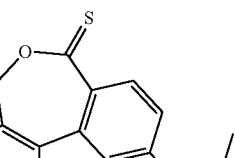<br>2S$^i$Pr-DOT Formula IV | 7.64 | Yellow crystalline solid; shows superior solubility in standard nail polish solution |
| 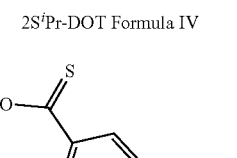<br>2S$^s$Bu-DOT | 2.00 | Orange oil; not bench stable; product appears cloudy and inhomogeneous in nail polish solution |

Statements

Statement 1. A polymer composition, comprising:
a first monomer of Formula I or a tautomer or salt thereof

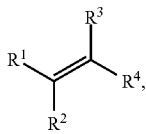

(I)

a second monomer comprising two or more non-aromatic unsaturated carbon-carbon bonds; and
a third monomer of Formula IV or a tautomer or salt thereof

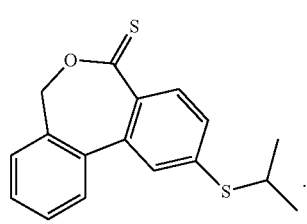

(IV)

Statement 2. The polymer composition of statement 1, wherein the first monomer is a methacrylate.

Statement 3. A cosmetic formulation comprising the polymeric composition of any one of statements 1 and 2 and a cosmetically acceptable excipient.

Statement 4. The polymer composition of any one of statements 1-3, wherein the first, second, and third monomer exist in about equal amounts in the polymer composition.

Statement 5. The polymer composition of any of statements 1-4, wherein the third monomer comprises 0.5-10 wt % of the polymer composition.

Statement 6. The polymer composition of any of statements 1-4, wherein the third monomer comprises 1-10 wt % of the composition.

Statement 7. A method of preparing the polymer composition of any one of statements 1-6, comprising:
mixing the first, second, and third monomers to form a first mixture; and irradiating the first mixture with ultraviolet light.

Statement 8. The method of statement 7, wherein the third monomer is added subsequently to the first and second monomers.

Statement 9. The method of any one of statements 7 or 8, further comprising the step of mixing the first, second, and third monomers on a proximal surface of the first mixture to form a second mixture; and
irradiating the second mixture with ultraviolet light.

Statement 10. A method of coloring a human's nails, comprising applying the polymer composition of any one statements 1-6 or the polymer prepared by any one statements 7-9 to a nail bed.

Statement 11. A method of removing a cosmetic, polymer composition from a nail bed, comprising:
immersing a nail bed coated with a polymer composition in a removal solution comprising cysteine and an aqueous base, the polymer composition comprising a first monomer;
a second monomer; and
a third monomer of Formula III or a tautomer or salt thereof

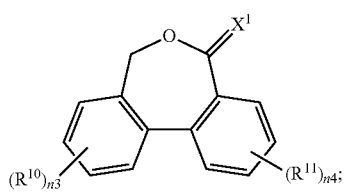

wherein $X^1$ is S or O;
each instance of $R^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —$OR^b$, —SCN, —$SR^b$, —$SSR^b$, —$N_3$, —NO, —$N(R^b)_2$, —$NO_2$, —C(=O)$R^b$, —C(=O)$OR^b$, —C(=O)$SR^b$, —C(=O)$N(R^b)_2$, —C(=$NR^b$)$R^b$, —C(=NR)$OR^b$, —C(=$NR^b$)$SR^b$, —C(=$NR^b$)$N(R)_2$, —S(=O)$R^b$, —S(=O)$OR^b$, —S(=O)$SR^b$, —S(=O)$N(R^b)_2$, —S(=O)$_2R^b$, —S(=O)$_2OR^b$, S(=O)$_2SR^b$, —S(=O)$_2N(R^b)_2$, —OC(=O)$R^b$, —OC(=O)$OR^b$, —OC(=O)$SR^b$, —OC(=O)$N(R^b)_2$, —OC(=$NR^b$)$R^b$, —OC(=$NR^b$)$OR^b$, —OC(=$NR^b$)$SR^b$, —OC(=$NR^b$)$N(R^b)_2$, —OS(=O)$R^b$, —OS(=O)$OR^b$, —OS(=O)$SR^b$, —OS(=O)$N(R^b)_2$, —OS(=O)$_2R^b$, —OS(=O)$_2OR^b$, —OS(=O)$_2SR^b$, —OS(=O)$_2N(R^b)_2$, —ON(R^b)$_2$, —SC(=O)$R^b$, —SC(=O)$OR^b$, —SC(=O)$SR^b$, —SC(=O)$N(R^b)_2$, —SC(=$NR^b$)$R^b$, —SC(=$NR^b$)$OR^b$, —SC(=$NR^b$)$SR^b$, —SC(=$NR^b$)$N(R^b)_2$, —N=$R^bC$(O)$R^b$, —$N^bC$(=O)$OR^b$, —$NR^bC$(=O)$SR^b$, —$NR^bC$(=O)$N(R^b)_2$, —$R^bC$(=$NR^b$)$R^b$, —$NR^bC$(=$NR^b$)$OR^b$, —$NR^bC$(=$NR^b$)$SR^b$, —$NR^bC$(=$NR^b$)$N(R^b)_2$, —$NR^bS$(=O)$R^b$, $NR^bS$(=O)$OR^b$, —$NR^bS$(=O)$SR^b$, —$NR^bS$(=O)$N(R^b)_2$, —$NR^bS$(=O)$_2R^b$, —$R^bS$(=O)$_2OR^b$, —$NR^bS$(=O)$_2SR^b$, —$NR^bS$(=O)$_2N(R^b)_2$, —Si($R^b$)$_3$, —Si($R^b$)$_2OR^b$, —Si($R^b$)($OR^b$)$_2$, —Si($OR^b$)$_3$, —OSi($R^b$)$_3$, —OSi($R^b$)$_2OR^b$, —OSi($R^b$)($OR^b$)$_2$, or —OSi($OR^b$)$_3$;
each instance of $R^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —$OR^b$, —SCN, —$SR^b$, —$SSR^b$, —$N_3$, —NO, —$N(R^b)_2$, —$NO_2$, —C(=O)$R^b$, —C(=O)$OR^b$, —C(=O)$SR^b$, —C(=O)$N(R^b)_2$, —C(=$NR^b$)$R^b$, —C(=NR)$OR^b$, —C(=$NR^b$)$SR^b$, —C(=$NR^b$)$N(R^b)_2$, —S(=O)$R^b$, —S(=O)$OR^b$, —S(=O)$SR^b$, —S(=O)$N(R^b)_2$, —S(=O)$_2R^b$, —S(=O)$_2OR^b$, —S(=O)$_2SR^b$, —S(=O)$_2N(R^b)_2$, —OC(=O)$R^b$, —OC(=O)$OR^b$, —OC(=O)SR, —OC(=O)$N(R^b)_2$, —OC(=$NR^b$)$R^b$, —OC(=$NR^b$)$OR^b$, —OC(=$NR^b$)$SR^b$, —OC(=$NR^b$)$N(R^b)_2$, —OS(=O)$R^b$, OS(=O)$OR^b$, —OS(=O)$SR^b$, OS(=O)$N(R^b)_2$, OS(=O)$_2R^b$, OS(=O)$_2OR^b$, OS(=O)$_2SR^b$, —OS(=O)$_2N(R^b)_2$, —ON($R^b$)$_2$, —SC(=O)$R^b$, —SC(=O)OR, —SC(=O)$SR^b$, —SC(=O)$N(R^b)_2$, —SC(=$NR^b$)R, —SC(=$NR^b$)$OR^b$, —SC(=$NR^b$)$SR^b$, —SC(=$NR^b$)$N(R^b)_2$, —$NR^bC$(=O)$R^b$, —$NR^bC$(=O)$OR^b$, —$NR^bC$(=O)$SR^b$, —$NR^bC$(=O)$N(R^b)_2$, —$NR^bC$(=$NR^b$)R, —$NR^bC$(=$NR^b$)$OR^b$, —$NR^bC$(=$NR^b$)$SR^b$, —$NR^bC$(=$NR^b$)$N(R^b)_2$, —$NR^bS$(=O)$R^b$, —$NR^bS$(=O)$OR^b$, —$NR^bS$(=O)$SR^b$, —$NR^bS$(=O)$N(R^b)_2$, —$NR^bS$(=O)$_2R^b$, —$NR^bS$(=O)$_2OR^b$, —$NR^bS$(=O)$_2SR^b$, —$N^bS$(=O)$_2N(R^b)_2$, —Si($R^b$)$_3$, —Si($R^b$)$_2OR^b$, —Si($R^b$)($OR^b$)$_2$, —Si($OR^b$)$_3$, —OSi($R^b$)$_3$, —OSi($R^b$)$_2OR^b$, —OSi($R^b$)($OR^b$)$_2$, or —OSi($OR^b$)$_3$;

n3 is 0, 1, 2, 3, or 4, n4 is 0, 1, 2, 3, or 4, and at least one of n3 and n4 is 1, 2, 3, or 4; provided that no instance of $R^{10}$ and $R^{11}$ comprises one or more non-aromatic unsaturated CC bonds.

Statement 12. The method of statement 11, where the nail bed is immersed for a period of about 5 to 10 minutes.

Statement 13. The method of any one of statements 11-12, wherein the removal solution further comprises acetone.

Statement 14. The method of any one of statements 11-13, wherein the third monomer is of Formula IV or a tautomer or salt thereof

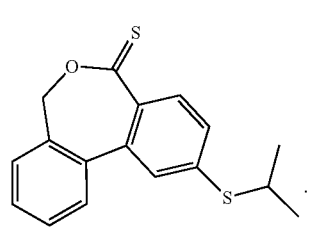

Statement 15. The method of any one of statements 11-14, wherein the first monomer is of Formula I or a tautomer or salt thereof

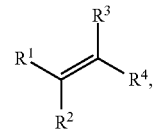

Statement 16. The method of any one of statements 11-15, wherein the removal solution comprises about 0.1 to 2 mM of cysteine.

Statement 17. The method of any one of statements 11-15, wherein the removal solution comprises about 0.1 to 0.5 mM of cysteine.

Statement 18. The method of any one of statements 11-17, wherein the removal solution has a pH of about 8-10.

Statement 19. A nail polish kit, comprising:
a nail polish composition, further comprising a first monomer, a second monomer, and a third monomer of Formula III or a tautomer or salt thereof:

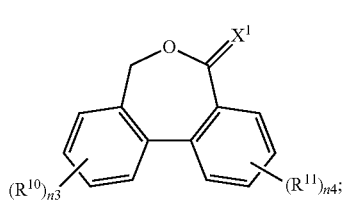

(III)

wherein:
X¹ is S or O;
each instance of $R^{10}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, —SCN, —SR$^b$, —SSR$^b$, —N$_3$, —NO, —N(R$^b$)$_2$, —NO$_2$, —C(=O)R$^b$, —C(=O)OR$^b$, —C(=O)SR$^b$, —C(=O)N(R$^b$)$_2$, —C(=NR$^b$)R$^b$, —C(=NR$^b$)OR$^b$, —C(=NR$^b$)SR$^b$, —C(=NR$^b$)N(R)$_2$, —S(=O)R$^b$, —S(=O)OR$^b$, —S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR, —OC(=O)N(R$^b$)$_2$, —OC(=NR$^b$)R$^b$, —OC(=NR)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR$^b$, —SC(=O)SR$^b$, —SC(=O)N(R$^b$)$_2$, —SC(=NR$^b$)R, —SC(=NR$^b$)OR$^b$, —SC(=NR$^b$)SR$^b$, —SC(=NR$^b$)N(R$^b$)$_2$, —NR$^b$C(=O)R$^b$, —NR$^b$C(=O)OR$^b$, —NR$^b$C(=O)SR$^b$, —NR$^b$C(=O)N(R$^b$)$_2$, —NR$^b$C(=ON)R$^b$, —NR$^b$C(=NR$^b$)OR$^b$, —NR$^b$C(=NR$^b$)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR$^b$, —OSi(R$^b$)(OR$^b$)$_2$, or —OSi(OR$^b$)$_3$;
each instance of $R^{11}$ is independently halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^b$, SCN, —SR$^b$, —SSR$^b$, —N$_3$, —NO, —N(R$^b$)$_2$, —NO$_2$, —C(=O)R, —C(=O)OR$^b$, —C(=O)SR$^b$, —C(=O)N(R$^b$)$_2$, —C(=NR$^b$)R$^b$, —C(=NR)OR$^b$, —C(=NR$^b$)SR$^b$, —C(=NR$^b$)N(R$^b$)$_2$, —S(=O)R$^b$, —S(=O)OR$^b$, —S(=O)SR$^b$, —S(=O)N(R$^b$)$_2$, —S(=O)$_2$R$^b$, —S(=O)$_2$OR$^b$, —S(=O)$_2$SR$^b$, —S(=O)$_2$N(R$^b$)$_2$, —OC(=O)R$^b$, —OC(=O)OR$^b$, —OC(=O)SR, —OC(=O)N(R$^b$)$_2$, —OC(=NR$^b$)R$^b$, —OC(=NR$^b$)OR$^b$, —OC(=NR$^b$)SR$^b$, —OC(=NR$^b$)N(R$^b$)$_2$, —OS(=O)R$^b$, —OS(=O)OR$^b$, —OS(=O)SR$^b$, —OS(=O)N(R$^b$)$_2$, —OS(=O)$_2$R$^b$, —OS(=O)$_2$OR$^b$, —OS(=O)$_2$SR$^b$, —OS(=O)$_2$N(R$^b$)$_2$, —ON(R$^b$)$_2$, —SC(=O)R$^b$, —SC(=O)OR$^b$, —SC(=O)SR$^b$, —SC(=O)N(R$^b$)$_2$, —SC(=NR$^b$)R$^b$, —SC(=NR$^b$)OR$^b$, —SC(=NR$^b$)SR$^b$, —SC(=NR$^b$)N(R$^b$)$_2$, —NR$^b$C(=O)R$^b$, —NR$^b$C(=O)OR$^b$, —NR$^b$C(=O)SR$^b$, —NR$^b$C(=O)N(R$^b$)$_2$, —NR$^b$C(=NR)R$^b$, —NR$^b$C(=NR)OR$^b$, —NR$^b$C(=NR)SR$^b$, —NR$^b$C(=NR$^b$)N(R$^b$)$_2$, —NR$^b$S(=O)R$^b$, —NR$^b$S(=O)OR$^b$, —NR$^b$S(=O)SR$^b$, —NR$^b$S(=O)N(R$^b$)$_2$, —NR$^b$S(=O)$_2$R$^b$, —NR$^b$S(=O)$_2$OR$^b$, —NR$^b$S(=O)$_2$SR$^b$, —NR$^b$S(=O)$_2$N(R$^b$)$_2$, —Si(R$^b$)$_3$, —Si(R$^b$)$_2$OR$^b$, —Si(R$^b$)(OR$^b$)$_2$, —Si(OR$^b$)$_3$, —OSi(R$^b$)$_3$, —OSi(R$^b$)$_2$OR$^b$, —OSi(R$^b$)(OR$^b$)$_2$, or —OSi(OR$^b$)$_3$, and
n3 is 0, 1, 2, 3, or 4, n4 is 0, 1, 2, 3, or 4; and at least one of n3 and n4 is 1, 2, 3, or 4; provided that no instance of $R^{10}$ and $R^{11}$ comprises one or more non-aromatic unsaturated CC bonds.
a removal solution comprising cysteine and an aqueous base; and instructions for using the nail polish kit.

Statement 20. The nail polish kit of statement 19, wherein the third monomer is Formula IV or tautomer or salt thereof

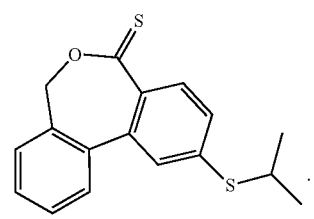

(IV)

Statement 21. The nail polish kit of any one of statements 19-20, wherein the removal solution comprises about 0.1 to 0.5 mM of cysteine.

Statement 22. The nail polish kit of any one of statements 19-21, wherein the nail polish composition comprises the first, second, and third monomers in about equal amounts in the polymer composition.

What is claimed is:
1. A polymer composition, comprising:
a first monomer of Formula I or a tautomer or salt thereof

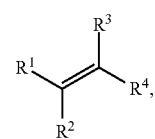

(I)

wherein $R^1$, $R^2$, and $R^3$ are independently selected from a group consisting of: hydrogen, halogen, or substituted or unsubstituted alkyl; and
$R^4$ is selected from a group consisting of: halogen, substituted or unsubstituted alkyl, substituted or unsubstituted carbocyclyl, substituted or unsubstituted heterocyclyl, substituted or unsubstituted aryl, substituted or unsubstituted heteroaryl, —CN, —OR$^a$—SCN, —SR$^a$—SSR$^a$—N$_3$, —NO, —N(R$^a$)$_2$, —NO$_2$, —C(=O)R$^a$, —C(=O)OR$^a$, —C(=O)SR$^a$, —C(=O)N(R$^a$)$_2$, —C(=NR$^a$)R$^a$, —C(=NR$^a$)OR$^a$, —C(=NR$^a$)SR$^a$, —C(=NR$^a$)N(R$^a$)$_2$, —S(=O)R$^a$, —S(=O)OR$^a$, —S(=O)SR$^a$, —S(=O)N(R$^a$)$_2$, —S(=O)$_2$R$^a$, —S(=O)$_2$OR$^a$, —S(=O)$_2$SR$^a$, —S(=O)$_2$N(R$^a$)$_2$, —OC(=O)R$^a$, OC(=O)OR$^a$, —OC(=O)SR$^a$, —OC(=O)N(R$^a$)$_2$, —OC(=NR$^a$)R$^a$, —OC(=NR$^a$)OR$^a$, OC(=NR$^a$)SR$^a$, OC(=NR$^a$)N(R$^a$)$_2$, —OS(=O)R$^a$—OS(=O)OR$^a$, —OS(=O)SR$^a$, —OS(=O)N(R$^a$)$_2$, —OS(=O)$_2$R$^a$, —OS(=O)$_2$OR$^a$, —OS(=O)$_2$SR$^a$, —OS(=O)$_2$N(R$^a$)$_2$, —ON(R$^a$)$_2$, —SC(=O)R$^a$, —SC(=O)OR$^a$, —SC(=O)SR$^a$, —SC(=O)N(R$^a$)$_2$, —SC(=NR$^a$)R$^a$, —SC(=NR$^a$)OR$^a$, —SC(=NR$^a$)SR$^a$, —SC(=NR$^a$)N(R$^a$)$_2$, —NR$^a$C(=O) R$^a$—NR$^a$C(=O)OR$^a$, —NR$^a$C(=O) SR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)SR$^a$, —NR$^a$C (=NR$^a$)N(R$^a$)$_2$, —NR$^a$S(=O)R$^a$, —NR$^a$S(=O)OR$^a$, —NR$^a$S(=O)SR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$SR$^a$, —NR$^a$S(=O)$_2$N(R$^a$)$_2$, —Si(R$^a$)$_3$, —Si(R$^a$)$_2$OR$^a$, —Si(R$^a$)(OR$^a$)$_2$, —Si(OR$^a$)$_3$, OSi(R$^a$)$_3$, —OSi(R$^a$)$_2$OR$^a$, —OSi(R$^a$)(OR$^a$)$_2$, or —OSi(OR$^a$)$_3$;

wherein each instance of R$^a$ is independently selected from a group consisting of hydrogen, substituted or unsubstituted alkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

a second monomer comprising two or more non-aromatic unsaturated carbon-carbon bonds; and a third monomer of Formula IV or a tautomer or salt thereof

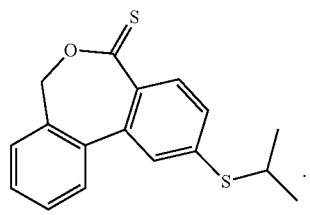

(IV)

2. The polymer composition of claim 1, wherein the first monomer is a methacrylate.

3. The polymer composition of claim 1, wherein the first, second, and third monomer exist in about equal amounts in the polymer composition.

4. The polymer composition of claim 1, wherein the polymer composition comprises 0.5-10 wt % of the third monomer.

5. The polymer composition of claim 1, wherein the polymer composition comprises 1-10 wt % of the third monomer.

6. The polymer composition of claim 1, wherein each of the alkyl, carbocyclyl, heterocyclyl, aryl, or heteroaryl groups are independently unsubstituted or substituted with one or more substituents independently selected from a group consisting of: halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR)R$^{bb}$, —SH, —SR$^{aa}$, —SSR$^{aa}$, —C(=O)R$^{aa}$, —CO$_2$H, —CHO, —C(OR$^{aa}$C)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^a$, —S(=O)R$^{aa}$, —OS(=O)R$^{aa}$, —Si(R$^a$a)$_3$, —OSi(R$^{aa}$)$_3$, —C(=S)N(R$^{bb}$)$_2$, —C(=O)SR$^{aa}$, —C(=S) SR$^{aa}$, —SC(=S)SR$^a$, —SC(=O)SR$^{aa}$, —OC(=O)SR$^{aa}$, —SC(=O)OR$^{aa}$, —SC(=O)R$^{aa}$, —P(=O)(R$^a$)$_2$, —P(=O)(OR$^{cc}$)$_2$, —OP(=O)(R$^{aa}$)$_2$, —OP(=O)(OR$^{cc}$C)$_2$, —P(=O)(N(R$^{bb}$)$_2$)$_2$, —OP(=O)(N(R$^b$)$_2$)$_2$, —NR$^{bb}$P(=O) (R$^a$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$+X$^-$, —P(OR)$_3$+X$^-$, —P(R$^{cc}$)$_4$, —P(OR)$_4$, —OP(R$^{cc}$)$_2$, —OP(R$^{cc}$)$_3$+X$^-$, —OP (OR$^{cc}$)$_2$, —OP(OR$^{cc}$)$_3$+X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group-O, —S, =NN(R$^{bb}$)$_2$, =NNR$^{bb}$C(=O)R$^{aa}$, =NNR$^{bb}$C(=O)OR$^{aa}$, =NNR$^{bb}$s(=O)$_2$R$^{aa}$, —NR$^{bb}$, or =NOR;

wherein each instance of R$^{aa}$ is independently selected from a group consisting of: C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

wherein each instance of R$^{bb}$ is independently selected from a group consisting of: hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$—C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O) SR$^{cc}$, —C(=S)SR$^{cc}$, —P(=O)(R$^{aa}$)$_2$, —P(=O) (OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

wherein each instance of Rec is independently selected from a group consisting of: hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two Rec groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

wherein each instance of R$^{dd}$ is independently selected from a group consisting of: halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$+X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC (=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$) OR$^{ee}$, —OC (=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O) SR$^{ee}$, —C(=S) SR$^{ee}$, —SC(=S) SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

wherein each instance of R$^{ee}$ is independently selected from a group consisting of: C$_{1-6}$ alkyl, C$_{1-6}$ perhaloalkyl, C$_{2-6}$ alkenyl, C$_{2-6}$ alkynyl, hetero C$_{1-6}$ alkyl, hetero C$_{2-6}$alkenyl, hetero C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

wherein each instance of R$^{ff}$ is independently selected from a group consisting of: hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and wherein each instance of R$^{gg}$ is independently selected from a group consisting of: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl) C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O) S(C$_{1-6}$ alkyl), —C(=S) SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents are joined to form =O or =S; and wherein X$^-$ is a counterion.

7. The polymer composition of claim 1, wherein the first monomer is selected from a group consisting of:

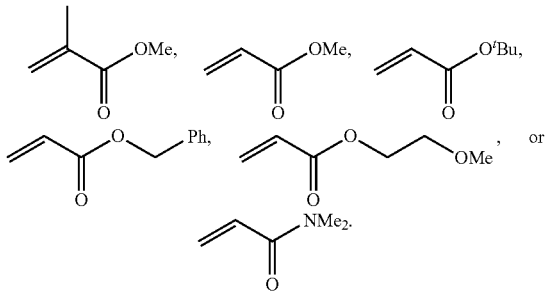

8. A cosmetic formulation comprising the polymeric-polymer composition of claim 1 and a cosmetically acceptable excipient.

9. A cosmetic formulation comprising the polymer composition of claim 2 and a cosmetically acceptable excipient.

10. A method of preparing the polymer composition of claim 1, comprising:
mixing the first, second, and third monomers to form a mixture, and polymerizing the mixture with ultraviolet irradiation.

11. The method of claim 10, wherein the third monomer is added subsequently to a first mixture of the first and second monomers.

12. A method of removably coating a surface with the polymer composition of claim 1, comprising:
applying a mixture comprising the first, second, and third monomers to a surface, and irradiating the mixture with ultraviolet light to form a coating on the surface.

13. The method of claim 12, further comprising:
applying a second mixture comprising the first, second, and third monomer to the coating on the surface, and irradiating the second mixture with ultraviolet light.

14. A method of removing a coating comprising the polymer composition of claim 1, comprising: immersing the coating in a removal solution comprising cysteine and an aqueous base.

15. The method of claim 14, wherein the removal solution further comprises acetone.

16. The method of claim 15, wherein the removal solution comprises about 0.1 to 2 mM of cysteine.

17. The method of claim 15, wherein the removal solution comprises about 0.1 to 0.5 mM of cysteine.

18. The method of claim 15, wherein the removal solution has a pH of about 8-10.

* * * * *